(12) United States Patent
Wu

(10) Patent No.: US 12,358,996 B2
(45) Date of Patent: Jul. 15, 2025

(54) FUSION PROTEINS FOR IMMUNOTHERAPY AGAINST CANCER AND INFECTIOUS DISEASES

(71) Applicant: NAVICURE BIOPHARMACEUTICALS LIMITED, Apia (WS)

(72) Inventor: Chia-Mao Wu, Hsinchu (TW)

(73) Assignee: NAVICURE BIOPHARMACEUTICALS LIMITED, Apia (WS)

( * ) Notice: Subject to any disclaimer, the term of this patent is extended or adjusted under 35 U.S.C. 154(b) by 0 days.

(21) Appl. No.: 18/826,183

(22) Filed: Sep. 6, 2024

(65) Prior Publication Data
US 2025/0011451 A1    Jan. 9, 2025

Related U.S. Application Data

(63) Continuation of application No. 17/240,160, filed on Apr. 26, 2021.
(Continued)

(51) Int. Cl.
C07K 16/28    (2006.01)
A61P 35/00    (2006.01)

(52) U.S. Cl.
CPC .......... C07K 16/2878 (2013.01); A61P 35/00 (2018.01); *C07K 2317/565* (2013.01);
(Continued)

(58) Field of Classification Search
CPC .......... C07K 16/2878; C07K 2317/565; C07K 2317/622; C07K 2319/01; C07K 2319/55; A61P 35/00
See application file for complete search history.

(56) References Cited

U.S. PATENT DOCUMENTS 8,119,117 B2 * 2/2012 Deisseroth ............. A61K 39/12
435/320.1
8,450,460 B2    5/2013 Hill et al.
(Continued)

FOREIGN PATENT DOCUMENTS

WO    2004044176 A2    5/2004
WO    2018052854 A1    3/2018
WO    2018213747 A1    11/2018

OTHER PUBLICATIONS

International Search Report for PCT/US2021/029203, dated Apr. 10, 2021.
(Continued)

*Primary Examiner* — Meera Natarajan
*Assistant Examiner* — Francesca Edgingtongiordano
(74) *Attorney, Agent, or Firm* — Hsiu-Ming Saunders; INTELLECTUAL PROPERTY CONNECTIONS, INC.

(57) ABSTRACT

Fusion proteins for immunotherapy against cancer and infectious diseases are disclosed. A fusion protein according to the invention comprises a CD40-binding domain; an antigen; and a translocation domain located between the CD40-binding domain and the antigen, in which a furin and/or cathepsin L cleavage site is present in the fusion protein between the CD40-binding domain and the translocation domain. The antigen is an antigen of a pathogen or a tumor antigen. The furin and/or cathepsin L cleavage site permits removal of the CD40-binding domain away from the fusion protein via furin and/or cathepsin L cleavage. Also disclosed are pharmaceutical compositions, expression vectors and use of the fusion proteins of the invention for eliciting an antigen-specific cell-mediated immune response, treating a tumor and/or a disease caused by a pathogen in a subject in need thereof.

20 Claims, 6 Drawing Sheets
Specification includes a Sequence Listing.

Related U.S. Application Data

(60) Provisional application No. 63/020,545, filed on May 6, 2020.

(52) U.S. Cl.
CPC .... *C07K 2317/622* (2013.01); *C07K 2319/01* (2013.01); *C07K 2319/55* (2013.01)

(56) References Cited

U.S. PATENT DOCUMENTS

| | | |
|---|---|---|
| 9,340,599 B2 | 5/2016 | Hill et al. |
| 9,481,714 B2 | 11/2016 | Wu et al. |
| 10,293,058 B2 | 5/2019 | Fotin-Mleczek et al. |
| 2007/0269409 A1 | 11/2007 | Deisseroth et al. |
| 2015/0368350 A1 | 12/2015 | Tykocinski et al. |
| 2016/0122412 A1 | 5/2016 | Stone et al. |
| 2017/0101636 A1 | 4/2017 | Poma et al. |
| 2018/0078636 A1 | 3/2018 | Wu et al. |

OTHER PUBLICATIONS

International Written Opinion for PCT/US2021/029203, dated Apr. 10, 2021.

\* cited by examiner

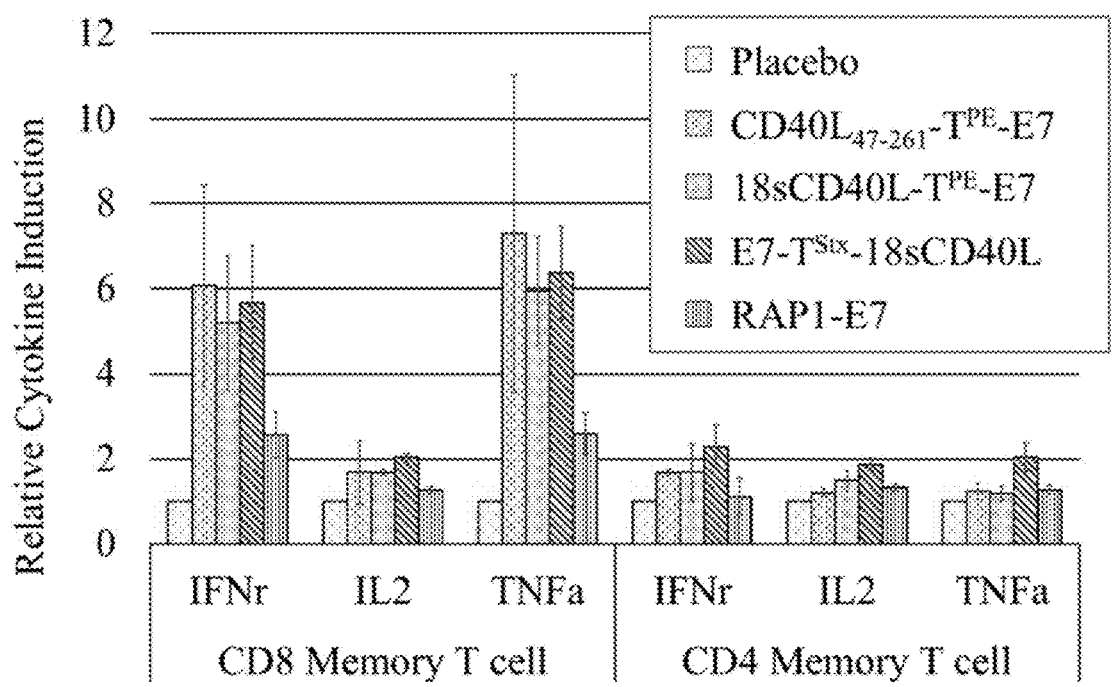

FIG. 10
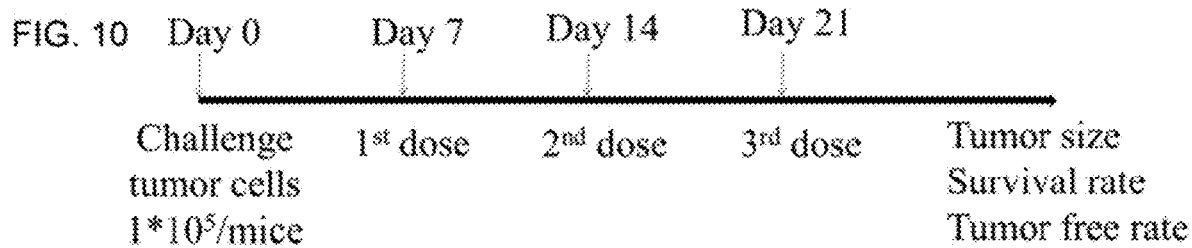
| Group | Fusion protein | Antigen (μg) | CpG1826 (μg) |
|---|---|---|---|
| A | Placebo | 0 | 0 |
| B | CD40L$_{47-261}$-T$^{PE}$-E7 | 25 | 50 |
| C | 18sCD40L-T$^{PE}$-E7 | 25 | 50 |
| D | E7-T$^{Stx}$-18sCD40L | 25 | 50 |
| E | RAP1-E7 | 25 | 50 |
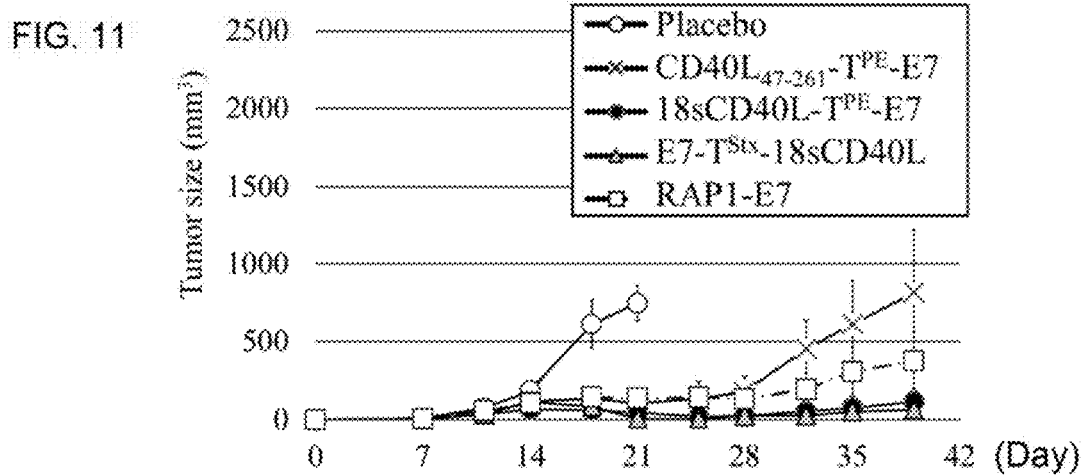
FIG. 11
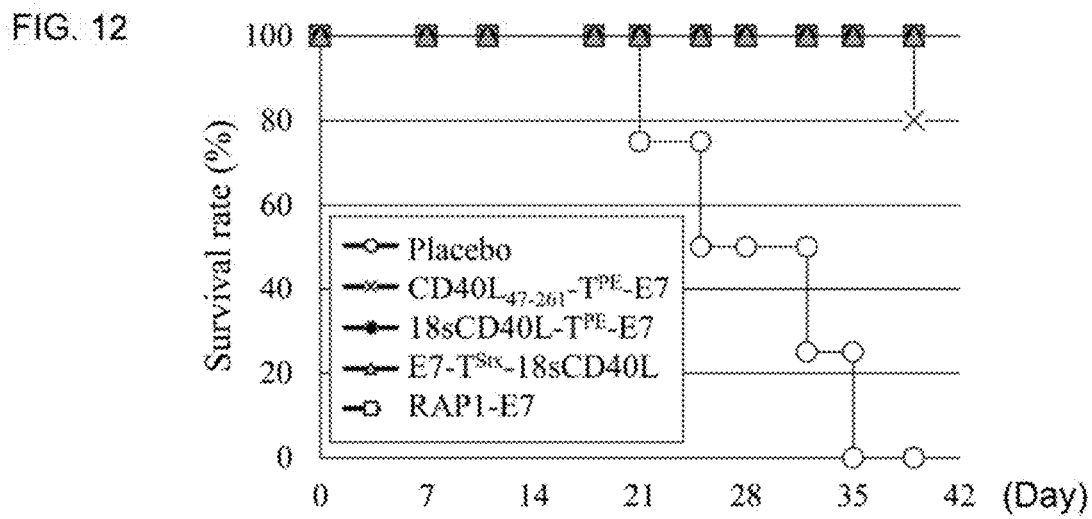
FIG. 12

FUSION PROTEINS FOR IMMUNOTHERAPY AGAINST CANCER AND INFECTIOUS DISEASES

REFERENCE TO RELATED APPLICATION

The present application is a continuation of and claims the priority to U.S. Ser. No. 17/240,160, filed Apr. 26, 2021, which status is pending and claims priority to U.S. Provisional Application Ser. No. 63/020,545, filed May 6, 2020, all of which are herein incorporated by reference in their entireties.

REFERENCE TO AN ELECTRONIC SEQUENCE LISTING

The contents of the electronic sequence listing (10040-001PCT_sequence listing_ST26_20241001 updated.xml; size 79 KB; creation date Oct. 1, 2024) are herein incorporated by reference in their entireties.

FIELD OF THE INVENTION

The present invention relates generally to fusion proteins, and more specifically to fusion proteins for eliciting T cell-mediated immune responses against tumors and infectious diseases.

BACKGROUND OF THE INVENTION

The adaptive immune system includes both humoral immunity components and cell-mediated immunity components and destroys invading pathogens. The cells that carry out the adaptive immune response are white blood cells known as lymphocytes. B cells and T cells, two different types of lymphocytes, carry out the main activities: antibody responses, and cell-mediated immune response. The adaptive immunity is activated by exposure to pathogens and leads to an enhanced immune response to future encounters with that pathogen. Vaccines induce antigen-specific memory in adaptive immune cells that enables protection against the target pathogen. There is still a need for novel therapeutic vaccines to treat diseases including cancer and infectious diseases caused by pathogens.

SUMMARY OF THE INVENTION

In one aspect, the invention relates to a fusion protein comprising: (a) a CD40-binding domain; (b) an antigen; and (c) a translocation domain located between the CD40-binding domain and the antigen; wherein a furin and/or cathepsin L cleavage site is present in the fusion protein between the CD40-binding domain and the translocation domain.

In another aspect, the invention relates to a DNA fragment encoding a fusion protein according to the invention. The invention also relates to an expressing vector comprising a DNA fragment encoding a fusion protein of the invention.

Further in another aspect, the invention relates to a pharmaceutical composition comprising a fusion protein of the invention and a pharmaceutical acceptable carrier and/or an adjuvant.

Yet in another aspect, the invention relates to a method for eliciting an antigen-specific cell-mediated immune response, comprising administering a therapeutically effective amount of the fusion protein of the invention to a subject in need thereof, and thereby eliciting an antigen-specific cell-mediated immune response in the subject in need thereof.

The invention also relates to a method for treating a tumor in a subject in need thereof, comprising administering to the subject in need thereof a therapeutically effective amount of the fusion protein of the invention, wherein the antigen of the fusion protein is a tumor antigen, and thereby treating the subject in need thereof.

The invention also relates to a method for treating a disease caused by a pathogen in a subject in need thereof, comprising administering to the subject in need thereof a therapeutically effective amount of the fusion protein of the invention, wherein the antigen of the fusion protein is an antigen of the pathogen, and thereby treating the disease caused by the pathogen.

BRIEF DESCRIPTION OF THE DRAWINGS

FIGS. 5A-E are schematic drawings illustrating various embodiments of the invention.
FIG. 6 is a graph showing relative cytokine inductions in each animal group.
FIG. 10 shows an immunization schedule and animal groups treated and untreated with the indicated fusion proteins, respectively.
FIG. 11 is a graph showing tumor size in each animal group treated or untreated with the fusion protein indicated.
FIG. 12 is a graph showing survival rate in each animal group treated or untreated with the fusion protein indicated.

DETAILED DESCRIPTION OF THE INVENTION

Figure 1:
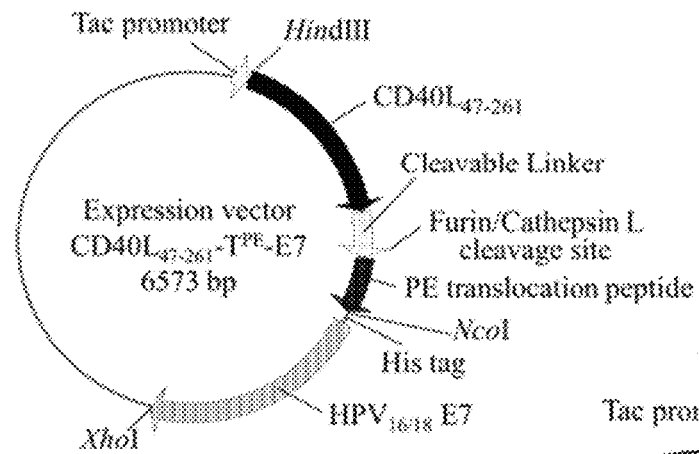
FIG. 1 is a vector map.

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definition

An antigen-presenting cell (APC) or accessory cell is a cell that displays antigen complexed with major histocompatibility complexes (MHCs) on their surfaces; this process is known as antigen presentation. T cells may recognize these complexes using their T cell receptors (TCRs). APCs process antigens and present them to T cells.

Antigen-presenting cells fall into two categories: professional and non-professional. Those that express MHC class II molecules along with co-stimulatory molecules and pattern recognition receptors are called professional antigen-presenting cells. The main types of professional antigen-presenting cells are dendritic cells (DCs), macrophages and B cells. The non-professional APCs express MHC class I molecules, which include all nucleated cell types in the body.

Professional APCs specialize in presenting antigens to T cells. They are very efficient at internalizing antigens, either by phagocytosis, or by receptor-mediated endocytosis, processing the antigen into peptide fragments and then displaying those peptides (bound to a class II MHC molecule) on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. All professional APCs also express MHC class I molecules as well.

Professional APCs and non-professional APCs use an MHC class I molecule to display endogenous peptides on the cell membrane. These peptides originate within the cell itself, in contrast to the exogenous antigen displayed by professional APCs using MHC class II molecules. Cytotoxic T cells are able to interact with antigens presented by the MHC class I molecule.

CD40 is a costimulatory protein expressed on antigen-presenting cells (e.g., dendritic cells, macrophages and B cells). The binding of CD40L to CD40 activates antigen-presenting cells and induces a variety of downstream effects. CD40 is a drug target for cancer immunotherapy.

The term "a CD40-binding domain" refers to a protein that can recognize and binds to CD40. A CD40-binding domain may be selected from one of the following: "CD40 ligand (CD40L) or a functional fragment thereof", "an anti-CD40 antibody or a functional fragment thereof."

The terms "CD40L", "CD40 ligand" and "CD154" are interchangeable. CD40L binds to CD40(protcin) on antigen-presenting cells (APC), which leads to many effects depending on the target cell type. CD40L plays a central role in co-stimulation and regulation of the immune response via T cell priming and activation of CD40-expressing immune cells. U.S. Pat. No. 5,962,406 discloses the nucleotide and amino acid sequence of CD40L.

The terms "anti-CD40 antibody" and "CD40-specific antibody" are interchangeable.

When the term "consist substantially of" or "consisting substantially of" is used in describing an amino acid sequence of a polypeptide, it means that the polypeptide may or may not have a starting amino acid "M" (translated from a start codon AUG) at N-terminal as a part of the polypeptide, depending on protein translation requirements. For example, when the antigen HPV 18E7 protein (SEQ ID NO: 39) fused to another polypeptide (e.g., another antigen), the starting amino acid "M" could be omitted or kept.

As used herein, "a translocation domain" is a polypeptide having biological activity in translocating an antigen within a fusion protein across an endosomal membrane into the cytosol of the CD40-expressing cell. The translocation domain guides or facilitates the antigen toward class I major histocompatibility complex (MHC-1) pathway (i.e., a cytotoxic T cell pathway) for antigen presentation.

The term "a *Pseudomonas* Exotoxin A (PE) translocation peptide ($T^{PE}$)" refers to a PE domain II peptide or a functional fragment thereof that has the biological activity in translocation.

The term "a Shiga toxin (Stx) translocation peptide ($T^{Stx}$)" refers to a Stx translocating domain or a functional fragment thereof that has the biological activity in translocation.

The terms "furin and/or cathepsin L" or "furin/cathepsin L" are interchangeable. A furin and/or cathepsin L cleavage site refers to a protease (furin and/or cathepsin L) sensitive site. It is a short peptide sequence that can be cleaved by furin or cathepsin L, or by both furin and cathepsin L. It may be a peptide linker comprising said cleavage site that is introduced into the fusion protein, or an intrinsic protease cleavage site present in the translocation domain of the fusion protein.

The terms "antigen" and "immunogen" are interchangeable. An antigen refers to an antigenic protein, which may be a tumor antigen (an antigen from a cancer or an antigen associated with a cancer), or an antigen of a pathogen (an antigen from a pathogen).

The terms "tumor" and "cancer" are interchangeable.

The terms "an antigen of a cancer cell" and "a tumor antigen" are interchangeable.

The term "a tumor antigen" refers to a tumor-specific antigen and/or a tumor-associated antigen. A tumor-associated antigen may be a protein or polypeptide expressed on the surface of a tumor cell.

Cluster of Differentiation 28 (CD28) is a T-cell-specific surface glycoprotein. A CD28 receptor is stimulated during the contact of T cells with antigen-presenting cells. Its function is involved in T-cell activation, the induction of cell proliferation and cytokine production and promotion of T-cell survival.

The term "an effective amount" refers to the amount of an active fusion protein that is required to confer a therapeutic effect on the treated subject. Effective doses will vary, as recognized by those skilled in the art, depending on rout of administration, excipient usage, and the possibility of co-usage with other therapeutic treatment.

The term "treating", or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

By "0 to 12 repeats" or "2 to 6 repeats", it means that all integer unit amounts within the range "0 to 12" or "2 to 6" are specifically disclosed as part of the invention. Thus, 0, 1, 2, 3, 4, . . . 10, 11and 12" or "2, 3, 4, 5 and 6" units amounts are included as embodiments of this invention.

In one aspect, the invention relates to a fusion protein comprising: (i) a CD40-binding domain; (ii) an antigen; and (iii) a translocation domain, located between the CD40-binding domain and the antigen, wherein a furin and/or cathepsin L cleavage site is present in the fusion protein between the CD40-binding domain and the translocation domain.

The fusion proteins of the invention can elicit an antigen-specific T cell immune response via MHC class I antigen presentation pathway. They share a common mechanism of action. Using the fusion protein 18sCD40L-$T^{PE}$-E7 as an example, the mechanism of action is illustrated below:

(1) the fusion protein binds to a CD40-expressing cell (e.g., dendritic cell or macrophage) and is internalized via a CD40-mediated endocytosis;

(2) the fusion protein is cleaved by furin protease and/or cathepsin L protease within the endosome so as to remove the 18sCD40L fragment away from the $T^{PE}$-E7 fragment;

(3) the $T^{PE}$-E7 fragment is translocated across the endosomal membrane of the endosome into the cytosol;

(4) the $T^{PE}$-E7 fragment is digested by cytosol proteasome to generate small E7 antigens with epitopes;

(5) the E7 antigens are delivered to MHC class I pathway for antigen presentation; and (6) a CD8+ T cell specific immune response is induced or enhanced by T-cell recognizing these presented antigens.

The above mechanism of action is applicable to the fusion protein E7-$T^{Stx}$-18sCD40L, in which case the furin and/or cathepsin L protease cleavage removes the E7-$T^{Stx}$ fragment away from the 18sCD40L fragment. Thus, the E7-$T^{Stx}$ fragment is translocated across the endosomal membrane of the endosome into the cytosol, digested by cytosol proteasome to generate small E7 antigens with epitopes; the E7 antigens delivered to MHC class I pathway for antigen presentation; and a CD8+ T cell specific immune response is induced or enhanced by T-cell recognizing these presented antigens.

According to the invention, no furin and/or cathepsin L cleavage site is present in the fusion protein between the antigen and the translocation domain.

The presence of the furin and/or cathepsin L cleavage site and its location in the fusion protein permits removal of the CD40-binding domain from the fusion protein after furin and/or cathepsin L cleavage.

In one embodiment, the fusion protein of the invention further comprises a peptide linker, said linker comprising the furin and/or cathepsin L cleavage site present in the fusion protein between the CD40-binding domain and the translocation domain.

The translocation domain and the antigen are located within the fusion protein in such an orientation and/or relation that permits the translocating domain to translocate the antigen across the membrane of the endosome and enter the cytosol, and then facilitate the antigen toward MHC class I pathway for antigen presentation in the CD40-expressing cell.

In one embodiment, the translocation domain is derived from a *Pseudomonas* Exotoxin A (PE). In another embodiment, the translocation domain is derived from a Shiga toxin (Stx).

In one embodiment, the translocation domain comprises or is a *Pseudomonas* Exotoxin A (PE) translocation peptide ($T^{PE}$), with the proviso that the CD40-binding domain is located at the N-terminal of the fusion protein.

In another embodiment, the translocation domain comprises or is a Shiga toxin (Stx) translocation peptide ($T^{Stx}$), with the proviso that the antigen is located at the N-terminal of the fusion protein.

In another embodiment, a fusion protein of the invention sequentially comprises: (i) a CD40-binding domain located at the N-terminal of the fusion protein; (ii) a translocation domain comprising a PE translocation peptide ($T^{PE}$); and (iii) an antigen located at the C-terminal of the fusion protein; wherein a furin and/or cathepsin L cleavage site is present in the fusion protein between the CD40-binding domain and the translocation domain.

In another embodiment, the translocation domain is a functional moiety of $T^{PE}$ and the furin and/or cathepsin L cleavage site is an intrinsic furin cleavage site from PE.

In another embodiment, a fusion protein of the invention sequentially comprises: (i) a CD40-binding domain located at the N-terminal of the fusion protein; (ii) a peptide linker comprising a furin and/or cathepsin L cleavage site; (iii) a translocation domain comprising a PE translocation peptide ($T^{PE}$); and (iv) an antigen of a pathogen or a tumor antigen.

In another embodiment, a fusion protein of the invention sequentially comprises: (i) an antigen located at the N-terminal of the fusion protein; (ii) a translocation domain comprising a Stx translocation peptide ($T^{Stx}$); and (iii) a CD40-binding domain; wherein a furin and/or cathepsin L cleavage site is present in the fusion protein between the CD40-binding domain and the translocation domain.

In one embodiment, the translocation domain is a functional moiety of $T^{Stx}$, and said furin and/or cathepsin L cleavage site is an intrinsic furin cleavage site from Stx.

Further in another embodiment, a fusion protein of the invention sequentially comprises: (i) an antigen located at the N-terminal of the fusion protein; (ii) a translocation domain comprising a Stx translocation peptide ($T^{Stx}$); (iii) a cleavable linker comprising a furin and/or cathepsin L cleavage site; and (iv) a CD40-binding domain.

In one embodiment, a furin and/or cathepsin L cleavage site comprises, or is, or consists of, an amino acid sequence of $RX^1X^2R$, wherein $X^1$ and $X^2$ are any amino acids, or comprise an amino acid sequence of $RX^1RX^2X^3R$, wherein $X^1$ and $X^2$ are any amino acids and $X^3$ is K, F or R.

In another embodiment, a PE translocation peptide ($T^{PE}$) is the domain II (amino acid residues 253-364; SEQ ID NO: 9) of *Pseudomonas* Exotoxin A protein (full-length PE, SEQ ID NO: 4).

In another embodiment, a PE translocation peptide ($T^{PE}$) comprises the minimal functional fragment GWEQLEQCGYPVQRLVALYLAARLSW (SEQ ID NO: 5).

In another embodiment, a PE translocation peptide ($T^{PE}$) consists of 26-112 amino acid residues in length, said the PE translocation peptide comprises a minimal functional fragment of GWEQLEQCGYPVQRLVALYLAARLSW (SEQ ID NO: 5).

In another embodiment, a PE translocation peptide ($T^{PE}$) comprises an amino acid sequence that is at least 90%, 95% or 99% identical to SEQ ID NO: 5, 6, 7, 8 or 9.

In another embodiment, a PE translocation peptide ($T^{PE}$) is selected from the group consisting of $PE_{280-305}$ (SEQ ID NO: 5), $PE_{280-313}$ (SEQ ID NO: NO: 6), $PE_{268-313}$ (SEQ ID NO: NO: 7), $PE_{253-313}$ (SEQ ID NO: 8), and $PE_{253-364}$ (SEQ ID NO: 9; full-length PE domain II).

In one embodiment, a Stx translocation peptide ($T^{Stx}$) is a functional fragment of Shiga toxin (Stx) subunit A (SEQ ID NO: 10) or Shiga-like toxin I (Slt-I) subunit A (SEQ ID NO: 11). According to the invention, a Stx translocation peptide has translocation function but no cytotoxic effect of subunit A. Sequence identify between Shiga toxin (Stx) subunit A and Slt-I subunit A is 99% and the two proteins has only one amino acid difference.

In another embodiment, a Stx translocation peptide ($T^{Stx}$) consists of 8-84 amino acid residues in length.

In another embodiment, a Stx translocation peptide ($T^{Stx}$) comprises a minimal functional fragment of LNCHHHAS (SEQ ID NO: 12).

In another embodiment, a Stx translocation peptide ($T^{Stx}$) consists of 8-84 amino acid residues in length, said $T^{Stx}$ comprising a minimal fragment of LNCHHHAS (SEQ ID NO: 12).

In another embodiment, a Stx translocation peptide ($T^{Stx}$) comprises an amino acid sequence that is at least 90%, 95% or 99% identical to the amino acid sequence selected from the group consisting of SEQ ID NOs: 12, 13, 14, 15 and 16.

In another embodiment, a Stx translocation peptide comprises an amino acid sequence selected from the group consisting of SEQ ID NOs: 12, 13, 14, 15 and 16.

In another embodiment, a Stx translocation peptide ($T^{Stx}$) is selected from the group consisting of $Stx_{240-247}$ (SEQ ID NO: 12), $Stx_{240-251}$ (SEQ ID NO: 13), $Stx_{211-247}$ (SEQ ID NO: 14), $Stx_{211-251}$ (SEQ ID NO: 15) and Stx $_{168-251}$ (SEQ ID NO: 16) of Stx subunit A.

A CD40-binding domain is a polypeptide having biological activity in binding to CD40 protein on a CD40-expressing cell. A CD40-binding domain permits a fusion protein of the invention to bind to a CD40 receptor on a CD40-expressing cell (e.g., dendritic cell or macrophage).

In one embodiment, a CD40-binding domain is selected from the group consisting of (i) a CD40 ligand (CD40L) or a functional fragment thereof; and (ii) an anti-CD40 antibody or a functional fragment thereof.

The CD40L, the anti-CD40 antibody, and the respective functional fragments thereof all have biological activity in binding to CD40 protein on a CD40-expressing cell. A functional fragment of CD40L is a truncated CD40L with biological activity, substantially lacking transmembrane and cytoplasmic regions of the full-length CD40L1-261 protein (SEQ ID NO: 17).

In another embodiment, a CD40L or a functional fragment thereof consists of 154-261 amino acid residues in length.

In another embodiment, a truncated CD40L with functional activity is selected from the group consisting of $CD40L_{47-261}$ (SEQ ID NO: 18) and $CD40L_{108-261}$ (named 18sCD40L; SEQ ID NO: 19).

In another embodiment, a CD40 ligand (CD40L) or a functional fragment thereof consists of 154-261 amino acid residues in length, said functional fragment thereof comprises $CD40L_{108-261}$ (SEQ ID NO: 19).

In another embodiment, a CD40L comprises or consists of an amino acid sequence that is at least 90%, 95% or 99% identical to SEQ ID NO: 17, 18 or 19, said CD40L having biological activity in binding to CD40 protein on a CD40-expressing cell.

In another embodiment, a CD40 ligand (CD40L) is selected from the group consisting of $CD40L_{47-261}$ (SEQ ID NO: 18), $CD40L_{108-261}$ (SEQ ID NO: 19; referred to as 18sCD40L) and $CD40L_{1-261}$ (SEQ ID NO: 17).

In another embodiment, a CD40-binding domain is a CD40-specific antibody (or anti-CD40antibody). A CD40-specific antibody is an antibody specific against CD 40 protein. A CD40-specific antibody can bind to CD40 protein on a CD40-expressing cell.

In one embodiment, the CD40-specific antibody comprises a heavy chain variable domain ($V_H$) and a light chain variable domain ($V_L$), wherein the $V_H$ comprises the amino acid sequence of SEQ ID NO: 22; and the $V_L$ comprises the amino acid sequence of SEQ ID NO: 23.

In another embodiment, the CD40-specific antibody according to the invention is selected from the group consisting of a single chain variable fragment (scFv), a diabody (dscFv), a triabody, a tetrabody, a bispecific-scFv, a scFv-Fc, a scFc-CH3, a single chain antigen-binding fragment (scFab), an antigen-binding fragment (Fab), $Fab_2$, a minibody and a fully antibody.

In another embodiment, a CD40-binding domain according to the invention is a CD40-specific scFv (anti-CD40 scFv) comprising a heavy chain variable domain ($V_H$), a light chain variable domain ($V_L$) and a flexible linker (L) connecting the $V_H$ and the $V_L$.

In one embodiment, a CD40-specific scFv comprises the amino acid sequence of SEQ ID NO: 20 or 21.

In another embodiment, the CD40-binding domain according to the invention is (i) a CD40-specific antibody or a binding fragment thereof, or (ii) a CD40-specific single chain variable fragment (scFv) or a binding fragment thereof; said CD40-specific antibody or said CD40-specific scFv comprising a $V_H$ and a $V_L$, wherein: (a) the $V_H$ comprises the amino acid sequence of SEQ ID NO: 22; and (b) the $V_L$ comprises the amino acid sequence of SEQ ID NO: 23.

In another embodiment, the CD40-specific antibody or CD40-specific scFv comprises a $V_H$ and a $V_L$, the $V_H$ comprising $V_H$ CDR1, $V_H$ CDR2 and $V_H$ CDR3; and the $V_L$ comprising $V_L$ CDR1, $V_L$ CDR2 and $V_L$ CDR3, wherein: (i) the $V_H$ CDR1, $V_H$ CDR2 and $V_H$ CDR3 comprises the amino acid sequence of SEQ ID NOs: 24, 25 and 26, respectively; and (ii) the $V_L$ CDR1, $V_L$ CDR2 and $V_L$ CDR3 comprises the amino acid sequence of SEQ ID NOs: 27, 28 and 29, respectively.

In another embodiment, the CD40-binding domain is a CD40-specific scFv comprising a $V_H$ and a $V_L$, wherein: (a) the $V_H$ comprises the amino acid sequence of SEQ ID NO: 22; and (b) the $V_L$ comprises the amino acid sequence of SEQ ID NO: 23.

In another embodiment, the fusion protein of the invention further comprises an endoplasmic reticulum (ER) retention sequence located at the C-terminal of the antigen, with the proviso that the translocation domain comprises a PE translocation peptide ($T^{PE}$).

In another embodiment, the ER retention sequence comprises an amino acid sequence selected from the group consisting of SEQ ID NO: 30, 31, 32, 33 and 34.

In another embodiment, the fusion protein of the invention further comprises a CD28-activating peptide located between the CD40-binding domain and the furin and/or cathepsin L cleavage site.

In another embodiment, the CD28-activating peptide consisting of 28-53 amino acid residues in length.

In another embodiment, the CD28-activating peptide has a length of 28-53 amino acid residues, said CD28-activating peptide comprising an amino acid sequence selected from the group consisting of SEQ ID NO: 35, 36 and 37.

In another embodiment, the CD28-activating peptide has a length of 28-53 amino acid residues, said CD28-activating peptide comprising the amino acid sequence of SEQ ID NO: 35.

In another embodiment, the CD28-activating peptide comprises an amino acid sequence selected from the group consisting of SEQ ID NO: 35, 36 and 37.

In another embodiment, the CD28-activating peptide comprises an amino acid sequence that is at least 90%, 95% or 99% identical to SEQ ID NO: 35, 36 or 37.

An antigen in the fusion protein of the invention is an antigen of a pathogen or a tumor antigen.

The pathogen may be selected from the group consisting of Human Papillomavirus (HPV), Human Immunodeficiency Virus-1 (HIV-1), Influenza Virus, Dengue Virus, Hepatitis A Virus (HAV), Hepatitis B Virus (HBV), Hepatitis C Virus (HCV), Hepatitis D Virus (HDV), Hepatitis E Virus (HEV), Severe acute respiratory syndrome-associated coronavirus (SARS-COV), Severe acute respiratory syndrome coronavirus 2 (SARS-COV-2), Middle East respiratory syndrome coronavirus (MERS-COV), Epstein-Barr virus (EBV), Zika Virus, Rabies Virus, Variola virus, Chikungunya Virus, West Nile virus, Poliovirus, Measles virus, Rubella virus, Hantavirus, Japanese encephalitis virus, Coxsackievirus, Echovirus, Enterovirus, Mumps virus, Varicella-zoster virus (VZV), Cercopithecine herpesvirus-1 (CHV-1), Yellow fever virus (YFV), Rift Valley Fever Virus, Lassa virus, Marburg virus, Ebolavirus, Norovirus, Rotavirus, Adenovirus, Sapovirus, Astrovirus, *Rickettsia prowazekii, Rickettsia typhi, Orientia tsutsugamushi, Borrelia burgdorferi, Yersinia pestis, Plasmodium vivax, Plasmodium malariae, Plasmodium falciparum, Plasmodium ovale, Bacillus anthracis, Clostridium Difficile, Clostridium Botulinum, Corynebacterium diphtheriae, Salmonella enterica serovar Typhi, Salmonella enterica serovar Paratyphi A, Shiga toxin-producing E. coli (STEC), Shigella dysenteriae, Shigella flexneri, Shigella boydii, Shigella sonnei, Entamoeba histolytica, Vibrio cholerae, Mycobacterium tuberculosis, Neisseria meningitidis, Bordetella pertussis, Haemophilus influenzae type B* (HiB), *Clostridium tetani, Listeria monocytogenes* and *Streptococcus pneumoniae*.

In another embodiment, the pathogen is selected from the group consisting of HPV, HIV-1, Influenza Virus, Dengue Virus, HAV, HBV, HCV, SARS-COV, SARS-COV-2. More particularly, the pathogen is selected from the group consisting of HPV, HBV, HCV and SARS-COV-2.

In another embodiment, the antigen is a pathogenic antigen selected from the group consisting of $HPV_{16}$ E7 protein, $HPV_{18}$ E7 protein, HBV X protein (HBx), HBV preS1 protein, HCV core protein (HCVcore) and SARS-COV-2 spike protein (CoV2S).

In another embodiment, said antigen comprises at least one epitope for inducing a desired immune response, preferably containing 1 to 30 epitopes, more preferably containing 1 to 15epitopes.

In another embodiment, the antigen is a pathogenic antigen comprising or consisting substantially of an amino acid sequence that is at least 70%, 80%, 90%, 95% or 99% identical to SEQ ID NO: 38, 39, 40, 41, 42 or 43.

In another embodiment, the antigen is a pathogenic antigen comprising or consisting substantially of an amino acid sequence that is at least 80% identical to SEQ ID NO: 38, 39, 40, 41, 42 or 43.

In another embodiment, the antigen comprises an amino acid sequence selected from the group consisting of SEQ ID Nos: 38, 39, 40, 41, 42 and 43.

In another embodiment, the antigen is a tumor antigen. A tumor antigen is a tumor-associated antigen (TAA) or a tumor-specific antigen (TSA).

In one embodiment, the tumor or cancer is selected from the group consisting of breast cancer, colon cancer, rectal cancer, bladder cancer, endometrial cancer, kidney cancer, gastric cancer, glioblastoma, hepatocellular carcinoma, bile duct cancer, small cell lung cancer, non-small cell lung cancer (NSCLC), melanoma, ovarian cancer, cervical cancer, pancreatic cancer, prostate cancer, acute myelogenous leukemia (AML), chronic myelogenous leukemia (CML), non-Hodgkin's lymphoma, and thyroid cancer.

In another embodiment, a tumor-associated antigen is selected from the group consisting of SSX2, MAGE-A3, NY-ESO-1, iLRP, WT12-281, RNF43, CEA-NE3, AFP, ALK, Anterior gradient 2 (AGR2), BAGE proteins, β-catenin, brc-abl, BRCA1, BORIS, CA9, carbonic anhydrase IX, caspase-8, CD40, CDK4, CEA, CTLA4, cyclin-B1, CYPIB1, EGFR, EGFRvIII, ErbB2/Her2, ErbB3, ErbB4, ETV6-AML, EphA2, Fra-1, FOLRI, GAGE proteins (e.g., GAGE-1, -2), GD2, GD3, GloboH, glypican-3, GM3, gp100, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc16 (CA-125), MUM1, NA17, NY-BRI, NY-BR62, NY-BR85, NY-ES01, OX40, p15, p53, PAP, PAX3, PAX5, PCTA-1, PLACI, PRLR, PRAME, PSMA (FOLHI), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3.

In another embodiment, the antigen is a tumor-associated antigen selected from the group consisting of SSX2, MAGE-A3, NY-ESO-1, iLRP, WT12-281, RNF43 and CEA-NE3.

In another embodiment, the antigen is a tumor-associated antigen comprising an amino acid sequence that is at least 70%, 80%, 90%, 95% or 99% identical to SEQ ID NO: 44, 45, 46, 47, 48, 49or 50.

In another embodiment, the antigen is a tumor-associated antigen comprising an amino acid sequence selected from the group consisting of SEQ ID NOs: 44, 45, 46, 47, 48, 49 and 50.

An antigen may be a single antigen or an antigenic fragment thereof, or a fusion antigen comprising at least two antigens fused together. For example, an antigen may be a single antigen of $HPV_{16}$ E7 protein or a fusion antigen comprising $HPV_{16}$ E7 and $HPV_{18}$ E7 proteins. A fusion antigen may or may not have a linker connecting different antigens.

In another embodiment, the antigen is a fusion antigen having at least one linker connecting different antigens.

In another embodiment, the antigen is a fusion antigen having a rigid linker, $(EAAAAK)_n$, connecting different antigens, wherein n is an integer from 0-12, preferably from 2-6, more preferably from 3-4. In other words, the rigid linker comprises 0 to 12 repeats, 2 to 6 repeats or 3-4 repeats of the sequence EAAAAK (SEQ ID NO: 56).

In another embodiment, the fusion protein of the invention further comprises a rigid linker between the CD40-binding domain and the furin and/or cathepsin L cleavage site. The rigid linker may be a peptide liner comprising 0 to 12 repeats of the amino acid sequence EAAAAK (SEQ ID NO: 56).

The rigid linker may be $(EAAAAK)_n$, or (SEQ ID NO: $56)_n$, wherein n is an integer from 0-12, preferably from 2-6, more preferably from 3-4.

In another embodiment, the rigid linker comprises 2 to 6 repeats or 3-4 repeats of SEQ ID NO: 56.

In another embodiment, the fusion protein of the invention comprises, or consists substantially of, an amino acid sequence that is at least 90%, 95% or 99% identical to SEQ ID NO: 51, 52, 53, 54 or 55.

Further in another embodiment, the fusion protein of the invention comprises, or consists substantially of, an amino acid sequence selected from the group consisting of SEQ ID NOs: 51, 52, 53, 54 and 55.

In another aspect, the invention relates to a DNA fragment encoding a fusion protein of the invention. The invention also relates to an expressing vector comprising a DNA fragment encoding a fusion protein of the invention. The invention further relates to a pharmaceutical composition comprising a fusion protein of the invention and a pharmaceutically acceptable carrier and/or an adjuvant.

The pharmaceutical composition may be an enteral or a parenteral dosage form, suitable for transdermal, transmucosal, nasopharyngeal, pulmonary or direct injection, or for systemic (e.g., parenteral) or local (e.g., intratumor or intralesional injection) administration. Parenteral injection may be via intravenous, intraperitoneal, intramuscular, subcutaneous or intradermal routes.

Suitable adjuvants include, but not limited to, a saponin-based adjuvant or a Toll-like receptor (TLR) agonist adjuvant. A saponin-based adjuvant may be GPI-0100, Quil A or QS-21. A TLR agonist adjuvant may be Poly I: C, monophosphoryl lipid A (MPL) or CpG oligonucleotide (e.g., class A CpG: CpG1585, CpG2216 or CpG2336; class B CpG: CpG1668, CpG1826, CpG2006, CpG2007, CpG BW006 or CpG D-SL01; class C CpG: CpG2395, CpG M362 or CpG D-SL03). In one embodiment, the adjuvant is a CpG oligonucleotide.

The pharmaceutical composition may also be administered orally, e.g., in the form of tablets, coated tablets, dragées, hard and soft gelatine capsules.

The dosage of the fusion protein may vary, depending on the disease to be controlled, the age and the individual condition of the patient and the mode of administration. The dosage may be fitted to individual requirements in each particular case so as to obtain a therapeutically effective amount of the fusion protein of the invention to achieve a desired therapeutic response.

For adult patients, a single dosage of about 0.1 to 50 mg, especially about 0.1 to 5 mg, comes into consideration. Depending on severity of the disease and the precise pharmacokinetic profile, the fusion protein may be administered with one dosage unit per week, bi-week or month, and totally give 1 to 6 dosage units per cycle to satisfy such treatment.

In another aspect, the invention relates to use of the fusion protein or the pharmaceutical composition of the invention in the manufacture of a medicament for eliciting an antigen-specific T cell immune response, protecting against and/or treating an infectious disease or a tumor in a subject in need thereof.

Abbreviations: Rap1. Ras-proximate-I or Ras-related protein 1: CD40, Cluster of differentiation 40; CDR, Complementarity-determining region.

EXAMPLES

Animal Tumor Model

An $HPV_{16}$ E6-and E7-expressing tumor cell line from lung epithelial cells of C57BL/6 mice was used to establish a mouse $HPV_{16}$ tumor model for in vivo efficacy assays in the examples 6-8. The tumor cells were grown in RPMI 1640 medium containing FBS (10%) and penicillin/streptomycin/Amphotericin B (50 units/mL) at 37° C., 5% CO2.

SEQ ID NOs. and Components

TABLE 1

| SEQ ID No. | Component name or sequence (N → C) | Length (aa) |
|---|---|---|
| None | Cleavable linker 1<br>$RX^1X^2R$, wherein $X^1$ and $X^2$ are any amino acid residue. | 4 |
| None | Cleavable linker 2<br>$RX^1RX^2X^3R$, wherein $X^1$ and $X^2$ are any amino acid residue, and $X^3$ is K, F or R. | 6 |
| 3 | Rigid linker 1 $(EAAAAK)_3$ | 18 |
| 4 | Full length PE | 613 |
| 5 | PE translocation peptide ($PE_{280-305}$, minimal) | 26 |
| 6 | PE translocation peptide ($PE_{280-313}$) | 34 |
| 7 | PE translocation peptide ($PE_{268-313}$) | 46 |
| 8 | PE translocation peptide ($PE_{253-313}$) | 61 |

TABLE 1-continued

| SEQ ID No. | Component name or sequence (N → C) | Length (aa) |
|---|---|---|
| 9 | PE translocation peptide ($PE_{253-364}$) | 112 |
| 10 | Full length Shiga toxin (Stx) subunit A | 293 |
| 11 | Full length Shiga-like toxin I (Slt-I) subunit A | 293 |
| 12 | Stx translocation peptide ($Stx_{240-247}$, minimal) | 8 |
| 13 | Stx translocationpsptide ($Stx_{240-251}$) | 12 |
| 14 | Stx translocation peptide ($Stx_{211-247}$) | 37 |
| 15 | Stx translocation peptide ($Stx_{211-251}$) | 41 |
| 16 | Stx translocation peptide ($Stx_{168-251}$) | 84 |
| 17 | Full length CD40 ligand ($CD40L_{1-261}$) | 261 |
| 18 | Truncated CD40 ligand ($CD40L_{47-261}$) | 215 |
| 19 | Truncated CD40 ligand ($CD40L_{108-261}$, also referred to as 18sCD40L) | 154 |
| 20 | Anti-CD40 scFv ($V_H$-L-$V_L$) | 246 |
| 21 | Anti-CD40 scFv ($V_L$-L-$V_H$) | 246 |
| 22 | $V_H$ of the anti-CD40 scFv | 119 |
| 23 | $V_L$ of the anti-CD40 scFv | 112 |
| 24 | $V_H$ CDR1 GFTFSTYGMH | 10 |
| 25 | $V_H$ CDR2 GKGLEWLSYISGGSSYIFYADSVRGR | 26 |
| 26 | $V_H$ CDR3 CARILRGGSGMDL | 13 |
| 27 | $V_L$ CDR1 CTGSSSNIGAGYNVY | 15 |
| 28 | $V_L$ CDR2 GNINRPS | 7 |
| 29 | $V_L$ CDR3 CAAWDKSISGLV | 12 |
| 30 | ER retention sequence KDEL | 4 |
| 31 | ER retention sequence KKDLRDELKDEL | 12 |
| 32 | ER retention sequence KKDELRDELKDEL | 13 |
| 33 | ER retention sequence KKDELRVELKDEL | 13 |
| 34 | ER retention sequence KDELKDELKDEL | 12 |
| 35 | CD28 consensus sequence $T^1D^2I^3Y^4F^5C^6K^7X^8E^9X^{10}X^{11}Y^{12}P^{13}P^{14}P^{15}Y^{16}X^{17}D^{18}N^{19}E^{20}K^{21}S^{22}N^{23}G^{24}T^{25}I^{26}I^{27}H^{28}$, wherein $X^8$ is I or L, $X^{10}$ is V, F or A, $X^{11}$ is M or L, $X^{17}$ is L or I. | 28 |
| 36 | CD28-activating peptide (minimal) | 28 |
| 37 | CD28-activating peptide | 53 |
| 38 | Antigen $HPV_{16}$ E7 protein | 98 |
| 39 | Antigen $HPV_{18}$ E7 protein | 104 |
| 40 | Antigen HBV X protein (HBx; full length) | 154 |
| 41 | Antigen HBV preS1 protein | 108 |
| 42 | Antigen HCV core protein (full length) | 190 |
| 43 | Antigen SARS-CoV-2 spike protein | 1273 |
| 44 | Antigen SSX2 | 187 |
| 45 | Antigen MAGE-A3 | 314 |
| 46 | Antigen NY-ESO-1 | 180 |
| 47 | Antigen iLRP | 296 |
| 48 | Antigen WT12-281 | 279 |
| 49 | Antigen RNF43 | 406 |
| 50 | Antigen CEA-NE3 | 284 |
| 51 | Fusion protein $CD40L_{47-261}$-$T^{PE}$-E7 | 528 |
| 52 | Fusion protein 18sCD40L-$T^{PE}$-E7 | 467 |
| 53 | Fusion protein E7-$T^{Stx}$-$CD40L_{47-261}$ | 535 |
| 54 | Fusion protein E7-$T^{Stx}$-18sCD40L | 474 |
| 55 | Fusion protein HBx-preS1-$T^{Stx}$-18sCD40L | 541 |
| 56 | Rigid linker EAAAAK | 6 |

Flow cytometry. Splenocytes were stimulated with an antigenic stimulator for 2 hours at 37° C., followed by treating with 50 μg/mL of Brefeldin A and Monensin at 37° C. for 2 hours. The cells were harvested, washed with PBS containing 0.5% BSA, and stained with APC/Cy7-conjugated anti-CD3 antibody, PerCP/Cy5.5-conjugated anti-CD4 antibody, FITC-conjugated anti-CD8 antibody, PE-conjugated anti-CD44 antibody and APC-conjugated anti-CD62L antibody simultaneously. After wash, the cells were permeabilized, fixed and intracellularly stained with PE-conjugated anti-IFN-γ antibody, PE/Cy7-conjugated anti-IL-2 antibody and eFluor450-conjugated anti-TNF-a antibody simultaneously. The intracellular cytokine characterization (IFN-γ, IL-2 or TNF-a) of splenocytes with CD8+ or CD4+ memory T cell phenotypes (CD3+ $CD44^{hi}CD62L10$) were further analyzed by Gallios flow cytometer and Kaluza software.

Enzyme-linked immunospot (ELISpot) assay. Splenocytes were seeded in triplicate in a pretreated murine IFN-γ capturing 96-well plate (CTL IMMUNOSPOT®) at a cell density of 2×10$^5$ cells/well in the presence or absence of an antigenic stimulator. The cells were discarded after 24 hours of incubation at 37° C. After wash, the captured IFN-γ was detected by biotin-conjugated anti-murine IFN-γ antibody at room temperature for 2 hours and the IFN-γ-immunospots were developed according to the manufacturer's instructions. The scanning and counting of IFN-γ-immunospots was performed by IMMUNOSPOT® S5 Micro analyzer (CTL).

Indirect enzyme-linked immunosorbent assay (ELISA). Collected whole blood samples were left undisturbed at 4° C. for 30-60 minutes followed by centrifugation at 5,000g for 10 minutes to pellet the clot. The serum samples were stored at −20° C. The purified coating protein for antigen-specific antibody binding was diluted in guanidine coating buffer (2 M guanidine hydrochloride, 500mM Na$_2$HPO$_4$, 25 mM citrate, pH 4.0-4.4) and distributed into 96-well plate at 1 μg/well. After overnight incubation at 4° C., the 96-well plate was blocked with 1% BSA in PBS at 37° C. for 1 hour. The serum samples were thawed, and subsequently 10-fold serial diluted in PBS with 1% BSA. The coated protein was incubated with 100 μl of 1000-fold diluted serum sample at 37°° C. for 2 hours. After 4 times washing with phosphate buffered saline TWEEN®-20 (PBST), the antigen-specific antibodies were detected by horseradish peroxidase (HRP)-conjugated goat anti-mouse IgG (at a dilution of 1:10,000, Cat #31430, Thermo Fisher Science) at 37° C. for 30 minutes. Following 4 times of washing with PBST, the HRP-mediated color development was catalyzed in the presence of 100 μL of TMB substrate and quenched by 100 μL of 1 N HCl. The relative titers of antigen-specific antibody in the serum samples were determined by the absorbance at 450 nm.

Statistical analysis. The significance of all comparisons was calculated by using t-test, and results considered significant when p<0.05.

Example 1

Constructions of Expression Vectors for CD40L$_{47261}$-T$^{PE}$-E7 and 18sCD40L-T$^{PE}$-E7

FIGS. 5A-E illustrates various embodiments of the fusion protein according to the invention.

The fusion protein CD40L$_{47-261}$-T$^{PE}$-E7 (SEQ ID NO: 51; FIG. 5A) comprises (a) a truncated CD40 ligand CD40L$_{47-261}$ (SEQ ID NO: 18); (b) a cleavable linker comprising (EAAAAK)$_3$ (SEQ ID NO: 3) and RX$^1$RX$^2$X$^3$R (SEQ ID NO: 2) (wherein X$^1$ is A, X$^2$ is Y, X$^3$ is K); (c) a PE translocation peptide of SEQ ID NO: 5 (PE$_{280-305}$); and (d) a fusion antigen HPV$_{16\ 18}$ E7, comprising a HPV$_{16}$ E7 protein of SEQ ID NO: 38 and a HPV$_{18}$ E7 protein of SEQ ID NO: 39.

An expression vector for CD40L$_{47-261}$-T$^{PE}$-E7 (FIG. 1) is constructed as follows: A DNA fragment encoding $^{HindIII}$CD40L-Linker-PE$^{NcoI,\ XhoI,\ SalI}$, comprising the CD40L$_{47-261}$, the cleavable linker and the PE translocation peptide (PE$_{280-305}$), was PCR synthesized, digested by HindIII/SalI and then ligated into the plasmid pTAC-MAT-Tag-2 having HindIII/XhoI cutting sites to obtain the plasmid P07-His-pNC (FIG. 2). Then, a DNA fragment encoding a fusion antigen HPV$_{16/18}$ E7 carrying a His tag was inserted into the plasmid PO7-His-pNC (FIG. 2) via restriction enzymes NcoI/XhoI to generate the expression vector for the fusion protein CD40L$_{47-261}$-T$^{PE}$-E7 (FIG. 1).

A cleavable linker allows furin and/or cathepsin L protease to cut the fusion protein for releasing the T$^{PE}$-E7 fragment from the fusion protein.

Figure 2:
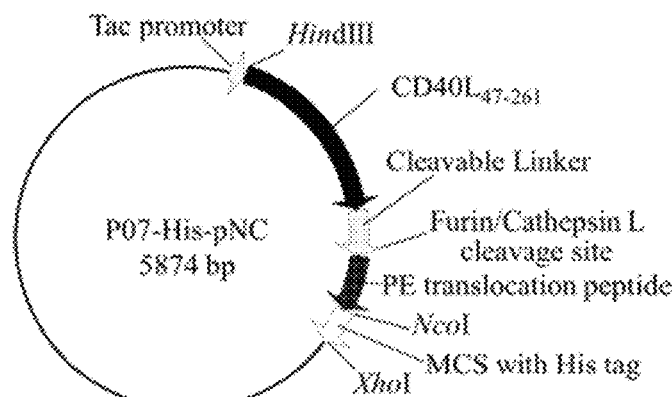
FIG. 2 is a vector map. MCS, multiple cloning sites.

Applying a similar method as described above, any other antigen(s) of interest may be used to replace E7 and be inserted into the plasmid of FIG. 2 to generate an expression vector similar to the plasmid of FIG. 1 for a fusion protein comprising the antigen of interest according to the invention.

An expression vector for the fusion protein 18sCD40L-T$^{PE}$-E7 (SEQ ID NO: 52; FIG. 5B) was constructed using a similar method described above, in which the truncated CD40 ligand: CD40L$_{47-261}$ (SEQ ID NO: 18) was replaced by 18sCD40L, another truncated CD40 ligand: CD40L$_{108261}$ (SEQ ID NO: 19).

Example 2

Construction of Expression Vectors for E7-T$^{Stx}$-CD40L$_{47-261}$ and E7-T$^{Stx}$-18sCD40L The fusion protein E7-T$^{Stx}$-CD40L$_{47-261}$ (SEQ ID NO: 53; FIG. 5C) comprises (a) a fusion antigen HPV$_{16/18}$ E7 (comprising HPV$_{16}$ E7 protein (SEQ ID NO: 38) and HPV$_{18}$ E7 protein (SEQ ID NO: 39)), (b) a Stx translocation peptide of SEQ ID NO: 14 (Stx$_{211-247}$), (c) a cleavable linker comprising RX$^1$X$^2$R (wherein X$^1$ is V, X$^2$ is A) and (EAAAAK)$_3$ of SEQ ID NO: 3, and (d) a truncated CD40 ligand of SEQ ID NO: 18 (CD40L$_{47-261}$).

Figure 3:
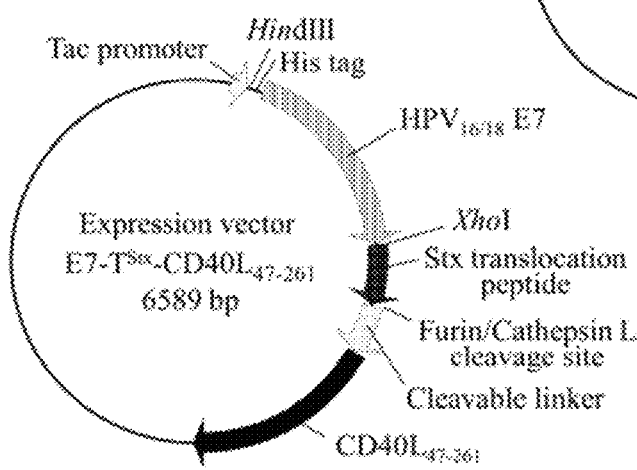
FIG. 3 is a vector map.
Figure 4:
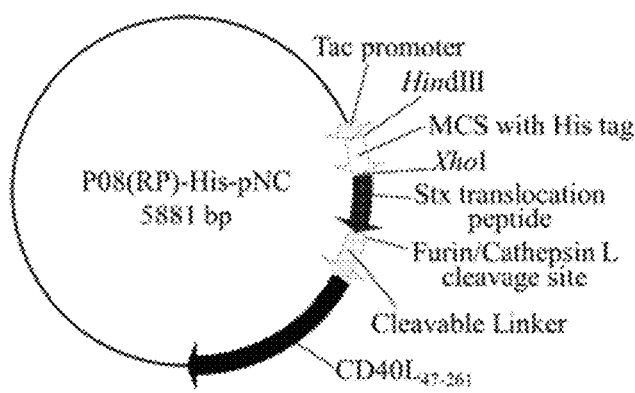
FIG. 4 is a vector map.

An expression vector for E7-T$^{Stx}$-CD40L$_{47-261}$ (FIG. 3) is constructed as follows:

A DNA fragment encoding $^{HindIII,\ XhoI}$Stx-Linker-CD40L$^{SalI}$, comprising the Stx translocation peptide (Stx$_{211-247}$), the cleavable linker and the CD40L$_{47-261}$, was PCR synthesized, digested by HindIII/Sa/I, then ligated into plasmid pTAC-MAT-Tag-2 backbone having HindIII/XhoI cutting sites to obtain the plasmid P08 (RP)-His-pNC (FIG. 4). Then, another DNA fragment encoding a fusion antigen HPV$_{16/18}$ E7 carrying a His tag was inserted into the plasmid P08 (RP)-His-pNC (FIG. 4) via restriction enzymes HindIII/XhoI to generate the expression vector E7-T$^{Stx}$-CD40L$_{47-261}$ (FIG. 3).

The cleavable linker is vital for the fusion protein of the invention because it allows the fusion protein to be cut by furin and/or cathepsin L protease so as to release the E7-T$^{Stx}$ fragment from the fusion protein. For example, see FIG. 5C.

Applying a similar method as described above, any other antigen(s) of interest from various pathogens or cancer may replace E7 and be inserted into the plasmid of FIG. 4 to generate an expression vector similar to the plasmid of FIG. 3 for a fusion protein comprising the antigen of interest according to the invention.

Using a similar method described above, an expression vector for the fusion protein E7-T$^{Stx}$-18sCD40L (SEQ ID NO: 54; FIG. 5D) was constructed, in which the truncated CD40 ligand: CD40L$_{47-261}$ (SEQ ID NO: 18) was replaced by 18sCD40L, another truncated CD40 ligand: CD40L$_{108-261}$ (SEQ ID NO: 19).

For a comparison purpose, we have constructed the fusion protein RAP1-CD28$_{conv}$PE$_t$-E7-K3 (referred to as "RAP1-E7" in the present application), which was almost identical to the prior construct disclosed in U.S. Pat. No. 9,481,714 B2, Example 1. The RAP1-CD28$_{conv}$PE$_t$-E7-K3 (referred as "RAP1-E7" in the application) comprises a RAPI domain III, a CD28 sequence, a linker, a PE translocation domain II (PE$_{268-313}$), an antigen E7 protein and an endoplasmic reticulum retention sequence. The antigen E7 protein used here is a fusion antigen HPV$_{16/18}$ E7, which comprises a HPV$_{16}$ E7 protein (SEQ ID NO: 38) and HPV$_{18}$ E7 protein (SEQ ID NO: 39), while the antigen E7 protein used in the prior art is HPV$_{16}$ E7 protein.

Example 3

Construction of Expression Vectors for HBx-preS1-T$^{Stx}$-18sCD40L

The fusion protein HBx-preS1-T$^{Stx}$-18sCD40L (SEQ ID NO: 55; FIG. 5E) comprises (a) a fusion antigen HBx-preS1 comprising a HBx protein of SEQ ID NO: 40 and a HBV preS1 protein of SEQ ID No. 41, (b) a Stx translocation peptide of SEQ ID NO: 14 (Stx$_{211-247}$), (c) a cleavable linker comprising RX$^1$X$^2$R (wherein X$^1$ is V, X$^2$ is A) and (EAAAAK)$_3$ of SEQ ID NO: 3, and (d) a truncated CD40 ligand of SEQ ID NO: 19 (18sCD40L).

Using a similar method described in Example 2, an expression vector for the fusion protein HBx-preS1-T$^{Stx}$-18sCD40L was constructed, in which the truncated CD40 ligand used was 18sCD40L and the antigen used was the fusion antigen HBx-preSI as described above.

Example 4

Protein Expression

*E. coli* BL21 cells harboring the protein expression vector CD40L$_{47-261}$-T$^{PE}$-E7 were inoculated in ZY media (10 g/L tryptone and 5 g/L yeast extract) containing a selected antibiotic at an appropriate concentration at 37° C. When the culture reached an early log phase, (OD$_{600}$=2 to 5), the expression of fusion protein was induced by isopropyl-1-thio-μ-D-galactopyranoside (IPTG) (0.5 to 2 mM). Cells were harvested after 4 hours of IPTG induction and disrupted by sonication. The inclusion bodies were isolated and solubilized in solubilization buffer (6 M guanidine hydrochloride, 20 mM potassium phosphate, 500 mM NaCl, 20 mM imidazole, 1 mM DTT, pH 7.4) for the recovery of overexpressed fusion protein. After purification, the refolding of the fusion protein was performed by dialysis against 20-to 50-fold volume of dialysis buffer (10 mM PBS) at 4° C. overnight. The refolded fusion proteins were subject to SDS-PAGE analyses under reduced (with dithiothreitol; +DTT) and non-reduced (without dithiothreitol; −DTT) conditions to evaluate whether they were properly refolded.

The following fusion proteins were also expressed and refolded by using a similar method as described above: (1) 18sCD40L-T$^{PE}$-E7; (2) E7-T$^{Stx}$-CD40L$_{47-261}$; (3) E7-T$^{Stx}$-18sCD40L; (4) RAP1-E7; (5) CD40L$_{47-261}$-T$^{PE}$-HBx-preS1; (6) 18sCD40L-T$^{PE}$-HBx-preS1; (7) HBx-preS1-T$^{Stx}$-CD40L47-261; (8) HBx-preS1-T$^{Stx}$-18sCD40L; (9) CD40L$_{47-261}$-T$^{PE}$-HCVcore; (10) 18sCD40L-T$^{PE}$-HCVcore; (11) HCVcore-T$^{Stx}$-CD40L47-261; (12) HCVcore-TStx-18sCD40L; (13) CD40L$_{47-261}$-T$^{PE}$-CoV2S; (14) 18sCD40L-T$^{PE}$-CoV2S; (15) CoV2S-TStx-CD40L47-261; (16) CoV2S-TStx-18sCD40L; (17) CD40L$_{47-261}$-TPE-SSX2; (18) 18sCD40L-T$^{PE}$-SSX2; (19) SSX2-T$^{Stx}$-CD40L$_{47-261}$; (20) SSX2-T$^{Stx}$-18sCD40L. The fusion proteins CD40L$_{47-261}$-TPF-E7, 18sCD40L-T$^{PE}$-E7, E7-T$^{Stx}$-18sCD40L, RAP1-E7 and HBx-preS1-T$^{Stx}$-18sCD40L were further subjected to an immunogenicity analysis or an efficacy analysis in the following experiments.

Example 5

Immunogenicity Analysis of Fusion Proteins

Female C57BL/6NCrlBltw mice (5 to 6-weck-old) were randomly divided into 5 groups (n=5): (A) placebo (i.e., PBS); (B) fusion protein CD40L$_{47-261}$-T$^{PE}$-E7 (100 μg); (C) fusion protein 18sCD40L-T$^{PE}$-E7 (100 μg); (D) fusion protein E7-T$^{Stx}$-18sCD40L (100 μg); and (E) fusion protein RAPI-E7 (100 μg). The fusion proteins were dialyzed into PBS. CpG1826 (50 μg) was used as an adjuvant to animal groups B to E. Each group received three immunizations subcutaneously (s.c.) at 7 days interval from day 0. Blood samples were collected on day 0, 7 and 14. On day 21, the blood samples were harvested and the splenocytes were resuspended in RPMI 1640 medium containing FBS (10%) and PSA.

The splenocytes were used to analyze intracellular cytokine induction (IFN-γ, IL-2 and TNF-α) in the CD8$^+$ and CD4$^+$ memory T cells in the presence or absence of antigen stimulation. Briefly, splenocytes from each animal group were treated with or without antigen E7 protein (2 μg/mL of HPV$_{16}$ E7 peptide pool) and then analyzed by flow cytometry. The degree or the level of the intracellular cytokine induction in each mouse group was presented as relative cytokine induction, which was obtained by normalizing the frequency of cytokine$^+$/CD8$^+$ and cytokine$^+$/CD4$^+$splenocytes in the presence of the stimulating antigen E7 to that of the unstimulated (untreated) control.

The splenocytes were also used to analyze the frequency of IFN-γ-secreting splenocytes in the presence or absence of antigen stimulation (2 μg/mL of HPV$_{16}$ E7 peptide pool) by using Enzyme-linked immunospot (ELISpot) assay. The results were presented as IFN-γ$^+$immunospots per million splenocytes.

The blood samples were used to analyze the level of serum HPV$_{16}$ E7-specific and HPV$_{18}$ E7-specific antibody by using ELISA, in which the purified HPV$_{16}$ E7 and HPV$_{18}$ E7 recombinant proteins were used as coating proteins, respectively.

FIG. 6 shows cytokine induction results after antigen stimulation of the splenocytes with HPV$_{16}$ E7 peptide pool. The relative cytokine induction of IFN-γ and TNF-α, but not IL2, in CD8$^+$memory T cells from the animals immunized with the fusion protein CD40L$_{47-261}$-T$^{PE}$-E7, 18sCD40L-T$^{PE}$-E7or E7-T$^{Stx}$-18sCD40L (Groups B-D) all significantly increased as compared to that from the RAP1-E7-treated group (Group E) or the placebo group (Group A). The relative cytokine induction of IL-2 in CD8 memory T cells, and the cytokines IFN-γ, IL-2 or TNF-α in CD4$^+$memory T cells in the animal groups B-E slightly increased, however, showed no significant difference as compared to placebo group (Group A).

Nonetheless, it can be concluded that the fusion protein of the invention is superior to the prior art fusion protein in inducing the expression of IFN-γ and TNF-α in CD8 memory T cells in response to the stimulation of the antigen HPV$_{16}$ E7.

Figure 7:
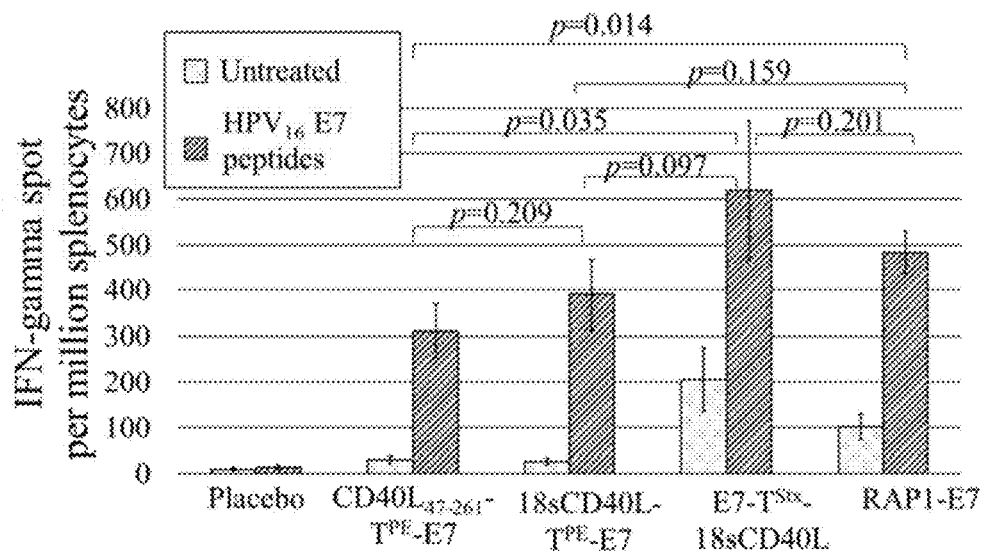
FIG. 7 is a graph showing IFN-$\gamma^+$ immunospots in the splenocytes from each animal group.

FIG. 7 shows IFN-γ$^+$ immunospots in the splenocytes stimulated with the HPV$_{16}$ E7 peptide pool in vitro. The frequency of IFN-γ-secreting splenocytes from the animal groups immunized with CD40L$_{47-261}$-T$^{PE}$-E7, 18sCD40L-T$^{PE}$-E7, E7-T$^{Stx}$-18sCD40L and RAP1-E7 (Groups B-E), respectively, significantly increased as compared to the placebo group. Particularly, E7-T$^{Stx}$-18sCD40L induced significantly higher frequency of IFN-γ-secreting cells than CD40L$_{47-261}$-T$^{PE}$-E7 (p=0.035).

The results indicate that the fusion protein of the invention can significantly increase IFN-γ-secreting T cell population upon or after stimulation with the antigenic HPV$_{16}$ E7 peptide pool.

Figure 8:
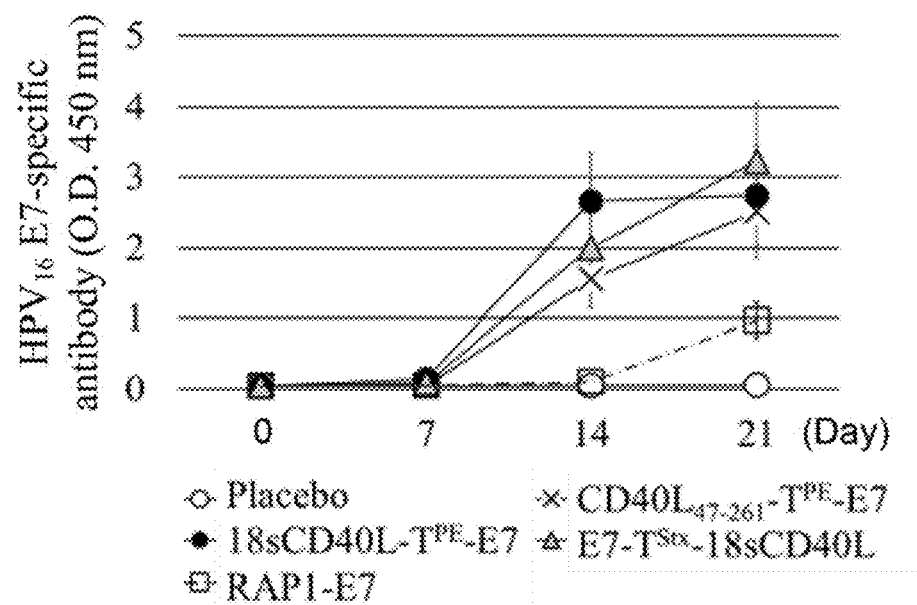
FIG. 8 is a graph showing serum $HPV_{16}$ E7-specific antibody level in each animal group.

FIG. 8 shows the serum HPV$_{16}$ E7-specific antibody levels in the animals immunized with various fusion proteins on day 0, 7 and 14. The HPV$_{16}$ E7-specific antibody level started to increase after the second vaccination on day 7, and further rose after the third vaccination on day 14 in animals vaccinated with CD40L$_{47-261}$-T$^{PE}$-E7, 18sCD40L-T$^{PE}$-E7 or E7-T$^{Stx}$-18sCD40L (Groups B-D respectively). On day 21, the serum HPV$_{16}$ E7-specific antibody levels in Groups B-D animals were higher than the placebo and the animal group vaccinated with RAP1-E7 (i.e., RAP1-CD28convPEt-E7-K3).

The fusion protein RAP1-E7 (RAP1-CD28convPEt-E7-K3) failed to elicit HPV 16 E7-specific antibody level after two vaccinations (on day 0 and 7). It started to induce HPV$_{16}$ E7-specific antibody after the third vaccination on day 14, and the serum antibody level was only modest on day 21 as compared to Groups B-D. In contrast, the fusion protein of the invention elicited serum HPV16 E7-specific antibody level after two shots of the vaccine on day 0 and 7.

A similar effect in inducing HBx-specific antibody was also observed when animals were vaccinated with RAP1-CD28convPEt-HBx-K3 (referred to as "RAP1-HBx"), using the same regimen and immunization schedule described above. The fusion protein RAP1-HBx was generated by using HBx antigen to replace the E7 antigen in the RAP1-E7 (RAP1-CD28convPEt-E7-K3). The fusion protein RAP1-HBx induced serum HBx-specific antibody level after the third vaccination on day 14, and the serum antibody level on day 21 was only modest as compared to animals vaccinated with the fusion protein of the invention (data not shown).

Figure 9:
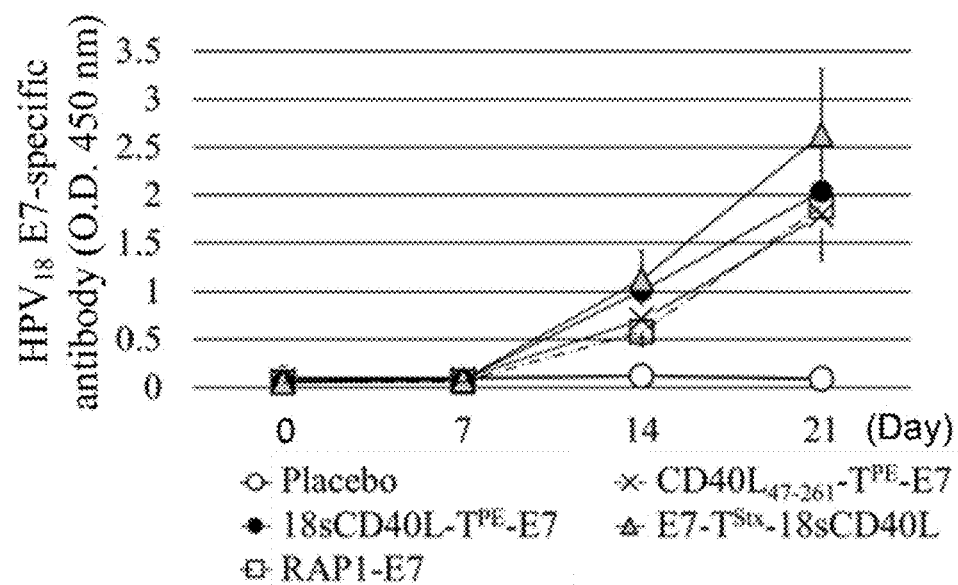
FIG. 9 is a graph showing serum $HPV_{18}$ E7-specific antibody level in each animal group.

FIG. 9 shows the serum HPV$_{18}$ E7-specific antibody level in the animals immunized with various fusion proteins on day 0, 7 and 14. The fusion proteins CD40L$_{47-261}$-T$^{PE}$-E7, 18sCD40L-T$^{PE}$-E7 and E7-T$^{Stx}$-18sCD40L (Groups B-D, respectively) significantly increased the serum HPV$_{18}$ E7-specific antibody level as compared to the placebo group.

Thus, the fusion protein of the invention is effective in inducing antigen-specific antibodies and the antibody induction occurs after twice vaccinations.

In summary, the fusion protein of the invention can induce antigen-specific T cell response, increase the expression of proinflammatory cytokines, e.g., IFN-γ and TNF-α, and generate antigen-specific antibody response.

Example 6

In Vivo Efficacy Assay of Fusion Proteins

Female C57BL/6NCrlBltw mice (5 to 6-week-old) were randomly divided into 5 groups and treated with PBS (Group A, placebo, n=4); or one of the following fusion proteins: Group B, CD40L$_{47-261}$-T$^{PE}$-E7 (25 μg; n=5); Group C, 18sCD40L-T$^{PE}$-E7 (25 μg; n=4); Group D, E7-T$^{Stx}$-18sCD40L (25 μg; n=5); and Group E, RAP1-E7 (25 μg; n=5). The fusion proteins were dissolved in PBS and CpG1826 (50 μg) was used as an adjuvant in vaccinating animals in Groups B to E. FIG. 10 shows an immunization schedule, fusion proteins and the dosages.

To challenge mice, tumor cells (1×10$^5$ in 0.1 mL) were injected s.c. into the left flank of each mouse on day 0. Three immunizations were s.c. given on day 7, 14 and 21. The tumor size was determined twice a week by multiplication of caliper measurements based on the modified ellipsoidal formula: Tumor volume=½ (length×width$^2$). The survival rate and tumor free rate were calculated. Mice with tumor length over 2 cm were considered dead and mice without measurable or palpable tumor masses were considered tumor-free.

The inoculated tumor developed rapidly in the placebo group, in which two animals died on day 25 and thus the data for the placebo group were shown only until day 21 (FIG. 11). The tumor masses in the Groups C and D animals (immunized with 18sCD40L-T$^{PE}$-E7 and E7-T$^{Stx}$-18sCD40L, respectively) were almost completely suppressed at least during the entire experimental period (last day is Day 39). The tumors in Group B and E animals (immunized with CD40L$_{47-261}$-T$^{PE}$-E7 and RAP1-E7, respectively) were initially well controlled, however, gradually grew after ceasing immunization.

The results indicate that the fusion protein of the invention, particularly the fusion proteins 18sCD40L-T$^{PE}$-E7 and E7-T$^{Stx}$-18sCD40L, can effectively suppress tumor growth.

The survival rate in the animal groups B-E (immunized with CD40L$_{47-261}$-T$^{PE}$-E7, 18sCD40L-T$^{PE}$-E7, E7-T$^{Stx}$-18sCD40L and RAP1-E7, respectively) remained 100% on day 35 as compared to the placebo group, which declined to 0% on day 35 (FIG. 12).

The results indicate that the fusion protein of the invention can effectively maintain the survival rate in the animal tumor model.

Figure 13:
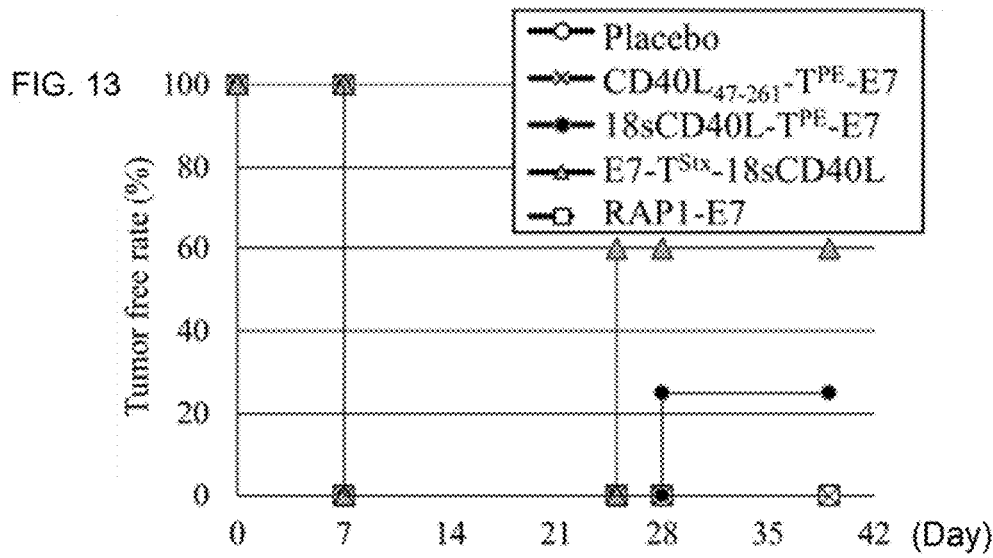
FIG. 13 is a graph showing tumor free rate in each animal group treated or untreated with the fusion protein indicated.

No tumor-free animals could be found in Groups A, B and E animals during the entire experimental period (day 39) (FIG. 13). One animal (25%) in group C and three animals (60%) in group D (immunized with 18sCD40L-T$^{PE}$-E7 and E7-T$^{Stx}$-18sCD40L, respectively) were found surviving without measurable or palpable tumors. Notably, in those tumor-free mice the tumor masses were all eliminated soon after completion of three times immunizations with 18sCD40L-T$^{PE}$-E7 or E7-TStx-18sCD40L.

The results indicated that the fusion proteins of the invention are more potent than the prior art fusion protein RAP1-E7 in increasing tumor free rate in animals having tumors.

Example 7

In Vivo Efficacy Analysis on Different Doses of 18sCD40L-T$^{PE}$-E7

Female C57BL/6NCrlBltw mice (4 to 6-week-old) were randomly divided into 5 groups (n=5per group): (A) placebo (PBS); (B) 18sCD40L-T$^{PE}$ (100 μg; without the fusion antigen E7); (C) 18sCD40L-T$^{PE}$-E7 (100 μg); (D) 18sCD40L-T$^{PE}$-E7 (50 μg); (E) 18sCD40L-T$^{PE}$-E7 (25 μg). The fusion proteins were dissolved in PBS and CpG1826 (50 μg) used as an adjuvant in Groups B to E. Tumor cells (1×10$^6$ in 0.1 mL) were injected s.c. into the left flank of each mouse on day 0. Two weeks after the challenge, tumor mice were vaccinated three times s.c. on day 14, 21 and 28.

Figure 14:
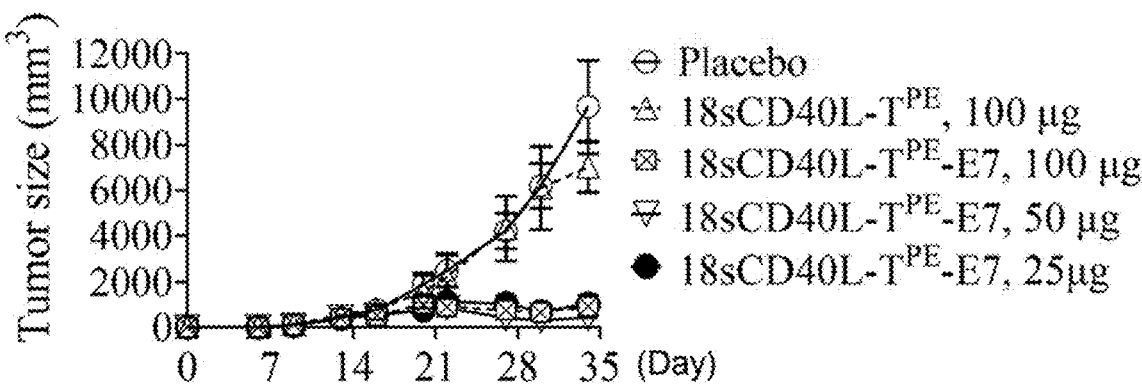
FIG. 14 is a graph showing tumor size in each animal group treated or untreated with the fusion protein 18sCD40L-$T^{PE}$-E7 at various doses indicated.

The tumor volume was determined. All the dosages (25 μg, 50 μg or 100 μg) of the fusion protein 18sCD40L-TPE-E7 showed potent effects in suppressing tumor growth. The inhibition of the tumor size by the fusion protein was seen after the first shot on day 14, sustained through the entire experimental period until the last day of observation on day 34. The placebo and 18sCD40L-T$^{PE}$, both lacking the antigen E7, had no effect in suppressing tumor growth (FIG. 14).

Example 8

In Vivo Efficacy Analysis on different doses of E7-T$^{Stx}$-18sCD40L

Figure 15:
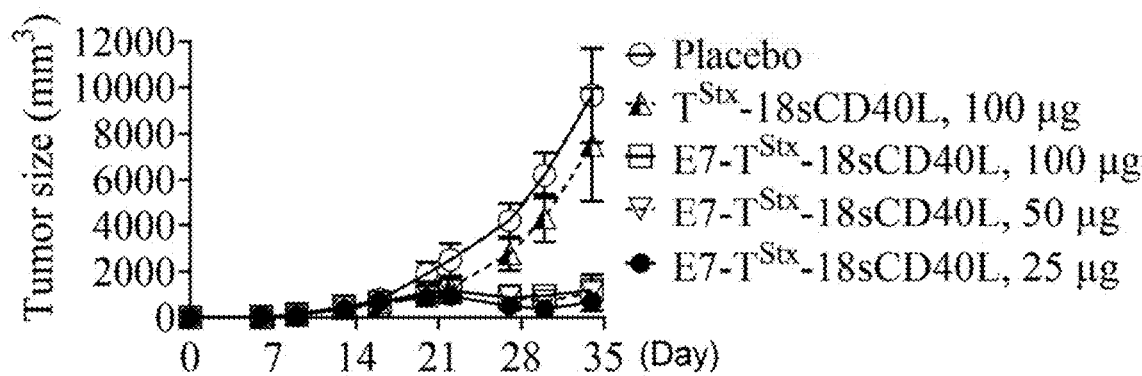
FIG. 15 is a graph showing tumor size in each animal group treated or untreated with the fusion protein E7-$T^{Stx}$-18sCD40L at various doses indicated.

Mice were grouped, challenged with tumor cells, and dosed on day 14, 21, 28 with the fusion protein, and the tumor size measured using a method similar to Example 7, except that Groups B-E mice were vaccinated with (B) T$^{Stx}$-18sCD40L (100 μg; without the fusion antigen E7); (C) E7-T$^{Stx}$-18sCD40L (100 μg); (D) E7-T$^{Stx}$-18sCD40L (50 μg); and (E) E7-TStx-18sCD40L (25 μg), respectively. All the dosages (25 μg, 50 μg or 100 μg) of the fusion protein E7-T$^{Stx}$-18sCD40L showed potent effects in suppressing tumor growth (FIG. 15). The inhibition of the tumor size by the fusion protein was seen after the first shot, sustained through the entire experimental period until the last day of observation on day 34. The placebo and T$^{Stx}$-18sCD40L, both lacking the antigen E7, had no effect in suppressing tumor growth (FIG. 15).

Thus, the fusion protein of the invention has potent effects in suppressing tumor growth with outstanding therapeutic efficacy.

Example 9

Figure 16:
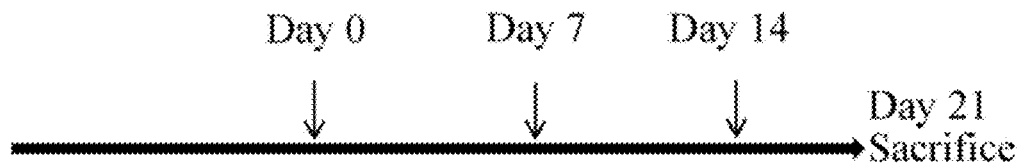
FIG. 16 shows an immunization scheme (upper panel), animal groups and respective dosing schedules (lower panel) of the fusion protein HBx-preS1-$T^{Stx}$-18sCD40L.

Number of Vaccine Doses: Immunogenicity Analysis of HBx-preS1-T$^{Stx}$-18sCD40L FIG. 16 shows each animal group's dosing schedule. C57BL/6JNarl female mice (5 weeks old) were randomly divided into four groups (n=5 per group): (1) placebo group; (2) DO-D7-D14 group (three doses, vaccinated on days 0, 7, 14); (3) D7-D14 (two doses, vaccinated on days 7, 14); and (4) D14 group (one dose, vaccinated on day 14). The placebo group received PBS via s.c. on Day 0, 7 and 14. Mice in other groups received HBx-preS1-T$^{Stx}$-18sCD40L (100 μg) adjuvanted with CpG1826 ODN (50 μg) via s.c. according to the dosing schedule in FIG. 16. Blood samples were collected on day 0, 7, 14 and 21. On day 21, the animals were sacrificed, splenocytes harvested and cultured. The frequency of IFN-γ-secreting splenocytes in the presence and absence of an antigenic stimulator (a HBx-specific peptide pool, i.e., HBV 32aa overlap 9 peptide) was analyzed by ELISpot assay, respectively. The levels of serum HBx-specific antibodies were assayed by ELISA, in which purified HBx recombinant proteins were used as coating proteins.

Figure 17:
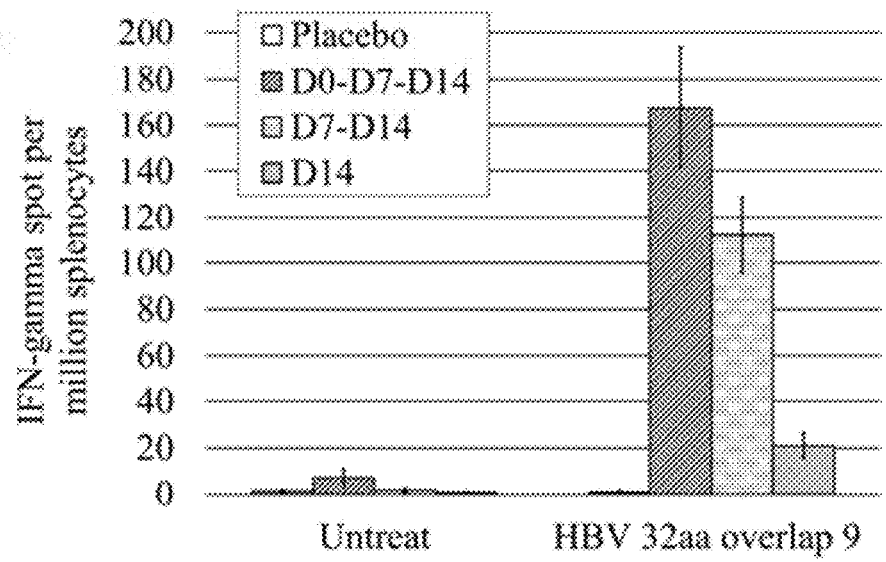
FIG. 17 is a graph showing IFN-$\gamma^+$ immunospots in the splenocytes from each animal group in FIG. 16.

FIG. 17 shows the IFN-γ$^+$ immunospots in the splenocytes stimulated with the HBV 32aa overlap 9 peptide pool in vitro in each animal group. The results indicate that the splenocytes from animal groups immunized with three doses, two doses and one dose (groups DO-D7-D14, D7-D14 and D14, respectively) all show a significant increase in the frequency of IFN-γ-secreting splenocytes as compared to the placebo. The frequency of IFN-γ-secreting splenocytes was positively correlated with the number of immunizations. The group DO-D7-D14 (vaccinated three times) showed the best induction of IFN-γ-secreting splenocytes.

Figure 18:
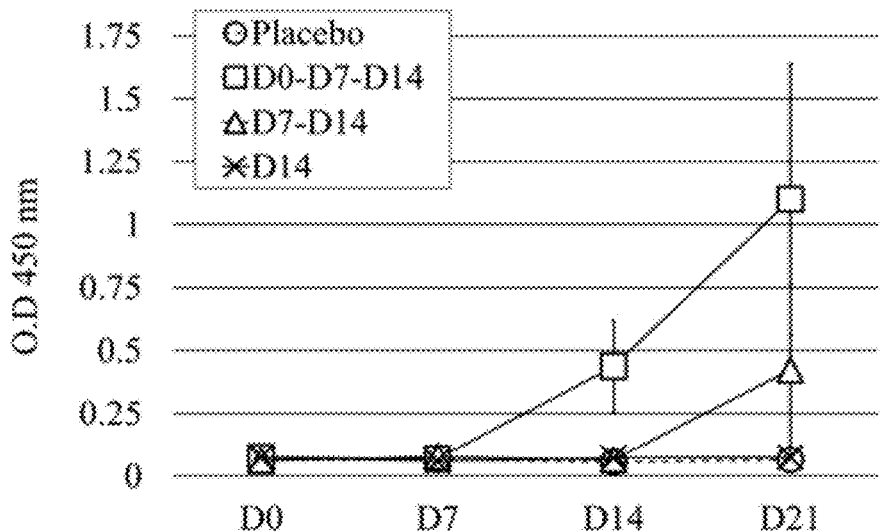
FIG. 18 is a graph showing serum HBx-specific antibody level in each animal group in FIG. 16.

In contrast, a single priming dose (D14 group) of HBx-preS1-T$^{Stx}$-18sCD40L did not apparently induce HBx-specific antibody response. However, the second immunization boosted the antibody level moderately (D7-D14 group) and the third dose further boosted the antibody level even higher as shown in the animal group DO-D7-D14 (FIG. 18). The dosing-number-dependent effect in inducing humoral response is consistent with that in inducing cell-mediated immune responses. The fusion protein is effective in inducing IFN-γ production in a dosing number dependent manner (FIG. 17).

Thus, the fusion protein HBx-preS1-T$^{Stx}$-18sCD40L could effectively elicit HBx-specific T cell-mediated immune response and HBx-specific humoral immune response after twice immunizations, which could be further boosted by multiple vaccinations.

The foregoing description of the exemplary embodiments has been presented only for the purposes of illustration and description and is not intended to be exhaustive to limit the invention to the precise forms disclosed. All references cited and discussed in this specification are incorporated herein by reference in their entireties and to the same extent as if each reference was individually incorporated by reference.

SEQUENCE LISTING

```
Sequence total quantity: 56
SEQ ID NO: 1              moltype =     length =
SEQUENCE: 1
000

SEQ ID NO: 2              moltype =     length =
SEQUENCE: 2
000

SEQ ID NO: 3              moltype = AA  length = 18
FEATURE                   Location/Qualifiers
REGION                    1..18
                          note = Rigid linker 1
source                    1..18
                          mol_type = protein
                          organism = synthetic construct
SEQUENCE: 3
EAAAAKEAAA AKEAAAAK                                                      18

SEQ ID NO: 4              moltype = AA  length = 613
FEATURE                   Location/Qualifiers
source                    1..613
                          mol_type = protein
                          organism = Pseudomonas aeruginosa
REGION                    1..613
```

```
                         note = Full length Pseudomonas Exotoxin A (PE)
SEQUENCE: 4
AEEAFDLWNE CAKACVLDLK DGVRSSRMSV DPAIADTNGQ GVLHYSMVLE GGNDALKLAI  60
DNALSITSDG LTIRLEGGVE PNKPVRYSYT RQARGSWSLN WLVPIGHEKP SNIKVFIHEL  120
NAGNQLSHMS PIYTIEMGDE LLAKLARDAT FFVRAHESNE MQPTLAISHA GVSVVMAQTQ  180
PRREKRWSEW ASGKVLCLLD PLDGVYNYLA QQRCNLDDTW EGKIYRVLAG NPAKHDLDIK  240
PTVISHRLHF PEGGSLAALT AHQACHLPLE TFTRHRQPRG WEQLEQCGYP VQRLVALYLA  300
ARLSWNQVDQ VIRNALASPG SGGDLGEAIR EQPEQARLAL TLAAAESERF VRQGTGNDEA  360
GAANADVVSL TCPVAAGECA GPADSGDALL ERNYPTGAEF LGDGGDVSFS TRGTQNWTVE  420
RLLQAHRQLE ERGYVFVGYH GTFLEAAQSI VFGGVRARSQ DLDAIWRGFY IAGDPALAYG  480
YAQDQEPDAR GRIRNGALLR VYVPRSSLPG FYRTGLTLAA PEAAGEVERL IGHPLPLRLD  540
AITGPEEEGG RLETILGWPL AERTVVIPSA IPTDPRNVGG DLAPSSIPDQ EQAISALPDY  600
ASQPGKPSRE DLK                                                    613

SEQ ID NO: 5             moltype = AA  length = 26
FEATURE                  Location/Qualifiers
REGION                   1..26
                         note = PE translocation peptide (PE280-305, minimal)
source                   1..26
                         mol_type = protein
                         organism = synthetic construct
SEQUENCE: 5
GWEQLEQCGY PVQRLVALYL AARLSW                                      26

SEQ ID NO: 6             moltype = AA  length = 34
FEATURE                  Location/Qualifiers
REGION                   1..34
                         note = PE translocation peptide (PE280-313)
source                   1..34
                         mol_type = protein
                         organism = synthetic construct
SEQUENCE: 6
GWEQLEQCGY PVQRLVALYL AARLSWNQVD QVIR                             34

SEQ ID NO: 7             moltype = AA  length = 46
FEATURE                  Location/Qualifiers
REGION                   1..46
                         note = PE translocation peptide (PE268-313)
source                   1..46
                         mol_type = protein
                         organism = synthetic construct
SEQUENCE: 7
PLETFTRHRQ PRGWEQLEQC GYPVQRLVAL YLAARLSWNQ VDQVIR                 46

SEQ ID NO: 8             moltype = AA  length = 61
FEATURE                  Location/Qualifiers
REGION                   1..61
                         note = PE translocation peptide (PE253-313)
source                   1..61
                         mol_type = protein
                         organism = synthetic construct
SEQUENCE: 8
GGSLAALTAH QACHLPLETF TRHRQPRGWE QLEQCGYPVQ RLVALYLAAR LSWNQVDQVI  60
R                                                                 61

SEQ ID NO: 9             moltype = AA  length = 112
FEATURE                  Location/Qualifiers
REGION                   1..112
                         note = PE translocation peptide (PE253-364)
source                   1..112
                         mol_type = protein
                         organism = synthetic construct
SEQUENCE: 9
GGSLAALTAH QACHLPLETF TRHRQPRGWE QLEQCGYPVQ RLVALYLAAR LSWNQVDQVI  60
RNALASPGSG GDLGEAIREQ PEQARLALTL AAAESERFVR QGTGNDEAGA AN          112

SEQ ID NO: 10            moltype = AA  length = 293
FEATURE                  Location/Qualifiers
source                   1..293
                         mol_type = protein
                         organism = Shigella dysenteriae
REGION                   1..293
                         note = Full length Shiga toxin (Stx) subunit A
SEQUENCE: 10
KEFTLDFSTA KTYVDSLNVI RSAIGTPLQT ISSGGTSLLM IDSGTGDNLF AVDVRGIDPE  60
EGRFNNLRLI VERNNLYVTG FVNRTNNVFY RFADFSHVTF PGTTAVTLSG DSSYTTLQRV  120
AGISRTGMQI NRHSLTTSYL DLMSHSGTSL TQSVARAMLR FVTVTAEALR FRQIQRGFRT  180
TLDDLSGRSY VMTAEDVDLT LNWGRLSSVL PDYHGQDSVR VGRISFGSIN AILGSVALIL  240
NCHHHASRVA RMASDEFPSM CPADGRVRGI THNKILWDSS TLGAILMRRT ISS         293
```

-continued

```
SEQ ID NO: 11          moltype = AA  length = 293
FEATURE                Location/Qualifiers
source                 1..293
                       mol_type = protein
                       organism = Escherichia coli
REGION                 1..293
                       note = Full length Shiga-like toxin I (Slt-I) subunit A
SEQUENCE: 11
KEFTLDFSTA KTYVDSLNVI RSAIGTPLQT ISSGGTSLLM IDSGSGDNLF AVDVRGIDPE  60
EGRFNNLRLI VERNNLYVTG FVNRTNNVFY RFADFSHVTF PGTTAVTLSG DSSYTTLQRV  120
AGISRTGMQI NRHSLTTSYL DLMSHSGTSL TQSVARAMLR FVTVTAEALR FRQIQRGFRT  180
TLDDLSGRSY VMTAEDVDLT LNWGRLSSVL PDYHGQDSVR VGRISFGSIN AILGSVALIL  240
NCHHHASRVA RMASDEFPSM CPADGRVRGI THNKILWDSS TLGAILMRRT ISS         293

SEQ ID NO: 12          moltype = AA  length = 8
FEATURE                Location/Qualifiers
REGION                 1..8
                       note = Stx translocation peptide (Stx240-247, minimal)
source                 1..8
                       mol_type = protein
                       organism = synthetic construct
SEQUENCE: 12
LNCHHHAS                                                           8

SEQ ID NO: 13          moltype = AA  length = 12
FEATURE                Location/Qualifiers
REGION                 1..12
                       note = Stx translocation peptide (Stx240-251)
source                 1..12
                       mol_type = protein
                       organism = synthetic construct
SEQUENCE: 13
LNCHHHASRV AR                                                      12

SEQ ID NO: 14          moltype = AA  length = 37
FEATURE                Location/Qualifiers
REGION                 1..37
                       note = Stx translocation peptide (Stx211-247)
source                 1..37
                       mol_type = protein
                       organism = synthetic construct
SEQUENCE: 14
PDYHGQDSVR VGRISFGSIN AILGSVALIL NCHHHAS                           37

SEQ ID NO: 15          moltype = AA  length = 41
FEATURE                Location/Qualifiers
REGION                 1..41
                       note = Stx translocation peptide (Stx211-251)
source                 1..41
                       mol_type = protein
                       organism = synthetic construct
SEQUENCE: 15
PDYHGQDSVR VGRISFGSIN AILGSVALIL NCHHHASRVA R                      41

SEQ ID NO: 16          moltype = AA  length = 84
FEATURE                Location/Qualifiers
REGION                 1..84
                       note = Stx translocation peptide (Stx168-251)
source                 1..84
                       mol_type = protein
                       organism = synthetic construct
SEQUENCE: 16
ALRFRQIQRG FRTTLDDLSG RSYVMTAEDV DLTLNWGRLS SVLPDYHGQD SVRVGRISFG  60
SINAILGSVA LILNCHHHAS RVAR                                         84

SEQ ID NO: 17          moltype = AA  length = 261
FEATURE                Location/Qualifiers
source                 1..261
                       mol_type = protein
                       organism = Homo sapiens
REGION                 1..261
                       note = Full length CD40 ligand (CD40L1-261)
SEQUENCE: 17
MIETYNQTSP RSAATGLPIS MKIFMYLLTV FLITQMIGSA LFAVYLHRRL DKIEDERNLH  60
EDFVFMKTIQ RCNTGERSLS LLNCEEIKSQ FEGFVKDIML NKEETKKENS FEMQKGDQNP  120
QIAAHVISEA SSKTTSVLQW AEKGYYTMSN NLVTLENGKQ LTVKRQGLYY IYAQVTFCSN  180
REASSQAPFI ASLCLKSPGR FERILLRAAN THSSAKPCGQ QSIHLGGVFE LQPGASVFVN  240
VTDPSQVSHG TGFTSFGLLK L                                            261
```

```
SEQ ID NO: 18           moltype = AA  length = 215
FEATURE                 Location/Qualifiers
REGION                  1..215
                        note = Truncated CD40 ligand (CD40L47-261)
source                  1..215
                        mol_type = protein
                        organism = synthetic construct
SEQUENCE: 18
HRRLDKIEDE RNLHEDFVFM KTIQRCNTGE RSLSLLNCEE IKSQFEGFVK DIMLNKEETK    60
KENSFEMQKG DQNPQIAAHV ISEASSKTTS VLQWAEKGYY TMSNNLVTLE NGKQLTVKRQ   120
GLYYIYAQVT FCSNREASSQ APFIASLCLK SPGRFERILL RAANTHSSAK PCGQQSIHLG   180
GVFELQPGAS VFVNVTDPSQ VSHGTGFTSF GLLKL                              215

SEQ ID NO: 19           moltype = AA  length = 154
FEATURE                 Location/Qualifiers
REGION                  1..154
                        note = Truncated CD40 ligand (CD40L108-261, also referred
                         to as 18sCD40L)
source                  1..154
                        mol_type = protein
                        organism = synthetic construct
SEQUENCE: 19
ENSFEMQKGD QNPQIAAHVI SEASSKTTSV LQWAEKGYYT MSNNLVTLEN GKQLTVKRQG    60
LYYIYAQVTF CSNREASSQA PFIASLCLKS PGRFERILLR AANTHSSAKP CGQQSIHLGG   120
VFELQPGASV FVNVTDPSQV SHGTGFTSFG LLKL                               154

SEQ ID NO: 20           moltype = AA  length = 246
FEATURE                 Location/Qualifiers
REGION                  1..246
                        note = Anti-CD40 scFv (VH-L-VL)
source                  1..246
                        mol_type = protein
                        organism = synthetic construct
SEQUENCE: 20
EVQLLESGGG LVQPGGSLRL SCAASGFTFS TYGMHWVRQA PGKGLEWLSY ISGGSSYIFY    60
ADSVRGRFTI SRDNSENALY LQMNSLRAED TAVYYCARIL RGGSGMDLWG QGTLVTVSSG   120
GGGSGGGGSG GGGSQSVLTQ PPSASGTPGQ RVTISCTGSS SNIGAGYNVY WYQQLPGTAP   180
KLLIYGNINR PSGVPDRFSG SKSGTSASLA ISGLRSEDEA DYYCAAWDKS ISGLVFGGGT   240
KLTVLG                                                              246

SEQ ID NO: 21           moltype = AA  length = 246
FEATURE                 Location/Qualifiers
REGION                  1..246
                        note = Anti-CD40 scFv (VL-L-VH)
source                  1..246
                        mol_type = protein
                        organism = synthetic construct
SEQUENCE: 21
QSVLTQPPSA SGTPGQRVTI SCTGSSSNIG AGYNVYWYQQ LPGTAPKLLI YGNINRPSGV    60
PDRFSGSKSG TSASLAISGL RSEDEADYYC AAWDKSISGL VFGGGTKLTV LGGGGGSGGG   120
GSGGGGSEVQ LLESGGGLVQ PGGSLRLSCA ASGFTFSTYG MHWVRQAPGK GLEWLSYISG   180
GSSYIFYADS VRGRFTISRD NSENALYLQM NSLRAEDTAV YYCARILRGG SGMDLWGQGT   240
LVTVSS                                                              246

SEQ ID NO: 22           moltype = AA  length = 119
FEATURE                 Location/Qualifiers
REGION                  1..119
                        note = VH of the anti-CD40 scFv
source                  1..119
                        mol_type = protein
                        organism = synthetic construct
SEQUENCE: 22
EVQLLESGGG LVQPGGSLRL SCAASGFTFS TYGMHWVRQA PGKGLEWLSY ISGGSSYIFY    60
ADSVRGRFTI SRDNSENALY LQMNSLRAED TAVYYCARIL RGGSGMDLWG QGTLVTVSS   119

SEQ ID NO: 23           moltype = AA  length = 112
FEATURE                 Location/Qualifiers
REGION                  1..112
                        note = VL of the anti-CD40 scFv
source                  1..112
                        mol_type = protein
                        organism = synthetic construct
SEQUENCE: 23
QSVLTQPPSA SGTPGQRVTI SCTGSSSNIG AGYNVYWYQQ LPGTAPKLLI YGNINRPSGV    60
PDRFSGSKSG TSASLAISGL RSEDEADYYC AAWDKSISGL VFGGGTKLTV LG           112

SEQ ID NO: 24           moltype = AA  length = 10
FEATURE                 Location/Qualifiers
```

```
                                          -continued

REGION                 1..10
                       note = VH CDR1
source                 1..10
                       mol_type = protein
                       organism = synthetic construct
SEQUENCE: 24
GFTFSTYGMH                                                              10

SEQ ID NO: 25          moltype = AA  length = 26
FEATURE                Location/Qualifiers
REGION                 1..26
                       note = VH CDR2
source                 1..26
                       mol_type = protein
                       organism = synthetic construct
SEQUENCE: 25
GKGLEWLSYI SGGSSYIFYA DSVRGR                                            26

SEQ ID NO: 26          moltype = AA  length = 13
FEATURE                Location/Qualifiers
REGION                 1..13
                       note = VH CDR3
source                 1..13
                       mol_type = protein
                       organism = synthetic construct
SEQUENCE: 26
CARILRGGSG MDL                                                          13

SEQ ID NO: 27          moltype = AA  length = 15
FEATURE                Location/Qualifiers
REGION                 1..15
                       note = VL CDR1
source                 1..15
                       mol_type = protein
                       organism = synthetic construct
SEQUENCE: 27
CTGSSSNIGA GYNVY                                                        15

SEQ ID NO: 28          moltype = AA  length = 7
FEATURE                Location/Qualifiers
REGION                 1..7
                       note = VL CDR2
source                 1..7
                       mol_type = protein
                       organism = synthetic construct
SEQUENCE: 28
GNINRPS                                                                 7

SEQ ID NO: 29          moltype = AA  length = 12
FEATURE                Location/Qualifiers
REGION                 1..12
                       note = VL CDR3
source                 1..12
                       mol_type = protein
                       organism = synthetic construct
SEQUENCE: 29
CAAWDKSISG LV                                                           12

SEQ ID NO: 30          moltype = AA  length = 4
FEATURE                Location/Qualifiers
REGION                 1..4
                       note = ER retention sequence
source                 1..4
                       mol_type = protein
                       organism = synthetic construct
SEQUENCE: 30
KDEL                                                                    4

SEQ ID NO: 31          moltype = AA  length = 12
FEATURE                Location/Qualifiers
REGION                 1..12
                       note = ER retention sequence
source                 1..12
                       mol_type = protein
                       organism = synthetic construct
SEQUENCE: 31
KKDLRDELKD EL                                                           12

SEQ ID NO: 32          moltype = AA  length = 13
```

```
FEATURE                 Location/Qualifiers
REGION                  1..13
                        note = ER retention sequence
source                  1..13
                        mol_type = protein
                        organism = synthetic construct
SEQUENCE: 32
KKDELRDELK DEL                                                          13

SEQ ID NO: 33           moltype = AA  length = 13
FEATURE                 Location/Qualifiers
REGION                  1..13
                        note = ER retention sequence
source                  1..13
                        mol_type = protein
                        organism = synthetic construct
SEQUENCE: 33
KKDELRVELK DEL                                                          13

SEQ ID NO: 34           moltype = AA  length = 12
FEATURE                 Location/Qualifiers
REGION                  1..12
                        note = ER retention sequence
source                  1..12
                        mol_type = protein
                        organism = synthetic construct
SEQUENCE: 34
KDELKDELKD EL                                                           12

SEQ ID NO: 35           moltype = AA  length = 28
FEATURE                 Location/Qualifiers
REGION                  1..28
                        note = CD28 consensus sequence
VAR_SEQ                 8
                        note = X is I or L
VAR_SEQ                 10
                        note = X is V, F or A
VAR_SEQ                 11
                        note = X is M or L
VAR_SEQ                 17
                        note = X is L or I
source                  1..28
                        mol_type = protein
                        organism = synthetic construct
SEQUENCE: 35
TDIYFCKXEX XYPPPYXDNE KSNGTIIH                                          28

SEQ ID NO: 36           moltype = AA  length = 28
FEATURE                 Location/Qualifiers
REGION                  1..28
                        note = CD28-activating peptide (minimal)
source                  1..28
                        mol_type = protein
                        organism = synthetic construct
SEQUENCE: 36
TDIYFCKIEV MYPPPYLDNE KSNGTIIH                                          28

SEQ ID NO: 37           moltype = AA  length = 53
FEATURE                 Location/Qualifiers
REGION                  1..53
                        note = CD28-activating peptide
source                  1..53
                        mol_type = protein
                        organism = synthetic construct
SEQUENCE: 37
NCDGKLGNES VTFYLQNLYV NQTDIYFCKI EVMYPPPYLD NEKSNGTIIH VKG               53

SEQ ID NO: 38           moltype = AA  length = 98
FEATURE                 Location/Qualifiers
source                  1..98
                        mol_type = protein
                        organism = Human papillomavirus type 16
REGION                  1..98
                        note = Antigen HPV16 E7 protein
SEQUENCE: 38
MHGDTPTLHE YMLDLQPETT DLYCYEQLND SSEEEDEIDG PAGQAEPDRA HYNIVTFCCK        60
CDSTLRLCVQ STHVDIRTLE DLLMGTLGIV CPICSQKP                               98

SEQ ID NO: 39           moltype = AA  length = 104
```

```
FEATURE                 Location/Qualifiers
source                  1..104
                        mol_type = protein
                        organism = Human papillomavirus type 18
REGION                  1..104
                        note = Antigen HPV18 E7 protein
SEQUENCE: 39
HGPKATLQDI VLHLEPQNEI PVDLLCHEQL SDSEEENDEI DGVNHQHLPA RRAEPQRHTM   60
LCMCCKCEAR IKLVVESSAD DLRAFQQLFL NTLSFVCPWC ASQQ                  104

SEQ ID NO: 40           moltype = AA   length = 154
FEATURE                 Location/Qualifiers
source                  1..154
                        mol_type = protein
                        organism = Hepatitis B virus
REGION                  1..154
                        note = Antigen HBV X protein (HBx; full length)
SEQUENCE: 40
MAARMCCQLD PARDVLCLRP VGAESRGRPL PGPLGALPPS SASAVPADHG SHLSLRGLPV   60
CSFSSAGPCA LRFTSARRME TTVNAPWSLP TVLHKRTIGL SGRSMTWIEE YIKDCVFKDW  120
EELGEEIRLK VFVLGGCRHK LVCSPAPCNF FTSA                             154

SEQ ID NO: 41           moltype = AA   length = 108
FEATURE                 Location/Qualifiers
source                  1..108
                        mol_type = protein
                        organism = Hepatitis B virus
REGION                  1..108
                        note = Antigen HBV preS1 protein
SEQUENCE: 41
MGGWSSKPRQ GMGTNLSVPN PLGFFPDHQL DPAFGANSNN PDWDFNPNKD HWPEANQVGA   60
GAFGPGFTPP HGGLLGWSPQ AQGILTTVPA APPPASTNRQ SGRQPTPI               108

SEQ ID NO: 42           moltype = AA   length = 190
FEATURE                 Location/Qualifiers
source                  1..190
                        mol_type = protein
                        organism = Hepatitis C virus
REGION                  1..190
                        note = Antigen HCV core protein (full length)
SEQUENCE: 42
MSTNPKPQRK TKRNTNRRPQ DVKFPGGGQI VGGVYLLPRR GPRLGVRATR KTSERSQPRG   60
RRQPIPKARR PEGRTWAQPG YPWPLYGNEG MGWAGWLLSP RGSRPNWGPT DPRRRSRNLG  120
KVIDTLTCGF ADLMGYIPLV GAPLGGVARA LAHGVRVLED GVNYATGNLP GCSFSIFLLA  180
LLSCLTTPAS                                                        190

SEQ ID NO: 43           moltype = AA   length = 1273
FEATURE                 Location/Qualifiers
REGION                  1..1273
                        note = Antigen SARS-CoV-2 spike protein
source                  1..1273
                        mol_type = protein
                        organism = Severe acute respiratory syndrome coronavirus 2
                        (SARS-CoV-2)
SEQUENCE: 43
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                  1273

SEQ ID NO: 44           moltype = AA   length = 187
```

```
FEATURE                 Location/Qualifiers
source                  1..187
                        mol_type = protein
                        organism = Homo sapiens
REGION                  1..187
                        note = Antigen SSX2
SEQUENCE: 44
MNGDDAFARR PTVGAQIPEK IQKAFDDIAK YFSKEEWEKM KASEKIFYVY MKRKYEAMTK    60
LGFKATLPPF MCNKRAEDFQ GNDLDNDPNR GNQVERPQMT FGRLQGISPK IMPKKPAEEG   120
NDSEEVPEAS GPQNDGKELC PPGKPTTSEK IHERSGPKRG EHAWTHRLRE RKQLVIYEEI   180
SDPEEDD                                                             187

SEQ ID NO: 45           moltype = AA   length = 314
FEATURE                 Location/Qualifiers
source                  1..314
                        mol_type = protein
                        organism = Homo sapiens
REGION                  1..314
                        note = Antigen MAGE-A3
SEQUENCE: 45
MPLEQRSQHC KPEEGLEARG EALGLVGAQA PATEEQEAAS SSSTLVEVTL GEVPAAESPD    60
PPQSPQGASS LPTTMNYPLW SQSYEDSSNQ EEEGPSTFPD LESEFQAALS RKVAELVHFL   120
LLKYRAREPV TKAEMLGSVV GNWQYFFPVI FSKASSSLQL VFGIELMEVD PIGHLYIFAT   180
CLGLSYDGLL GDNQIMPKAG LLIIVLAIIA REGDCAPEEK IWEELSVLEV FEGREDSILG   240
DPKKLLTQHF VQENYLEYRQ VPGSDPACYE FLWGPRALVE TSYVKVLHHM VKISGGPHIS   300
YPPLHEWVLR EGEE                                                     314

SEQ ID NO: 46           moltype = AA   length = 180
FEATURE                 Location/Qualifiers
source                  1..180
                        mol_type = protein
                        organism = Homo sapiens
REGION                  1..180
                        note = Antigen NY-ESO-1
SEQUENCE: 46
MQAEGRGTGG STGDADGPGG PGIPDGPGGN AGGPGEAGAT GGRGPRGAGA ARASGPGGGA    60
PRGPHGGAAS GLNGCCRCGA RGPESRLLEF YLAMPFATPM EAELARRSLA QDAPPLPVPG   120
VLLKEFTVSG NILTIRLTAA DHRQLQLSIS SCLQQLSLLM WITQCFLPVF LAQPPSGQRR   180

SEQ ID NO: 47           moltype = AA   length = 296
FEATURE                 Location/Qualifiers
source                  1..296
                        mol_type = protein
                        organism = Homo sapiens
REGION                  1..296
                        note = Antigen iLRP
SEQUENCE: 47
FSGALDVLQM KEEDVLKFLA AGTHLGGTNL DFQMEQYIYK RKSDGIYIIN LKRTWEKLLL    60
AARAIVAIEN PADVSVISSR NTGQRAVLKF AAATGATPIA GRFTPGTFTN QIQAAFREPR   120
LLVVTDPRAD HQPLTEASYV NLPTIALCNT DSPLRYVDIA IPCNNKGAAH SVGLMWWMLA   180
REVLRMRGTI SREHPWEVMP DLYFYRDPEE IEKEEQAAAE KAVTKEEFQG EWTAPAPEFT   240
ATQPEVADWS EGVQVPSVPI QQFPTEDWSA QPATEDWSAA PTAQATEWVG ATTDWS       296

SEQ ID NO: 48           moltype = AA   length = 279
FEATURE                 Location/Qualifiers
source                  1..279
                        mol_type = protein
                        organism = Homo sapiens
REGION                  1..279
                        note = Antigen WT12-281
SEQUENCE: 48
GSDVRDLNAL LPAVPSLGGG GGCALPVSGA AQWAPVLDFA PPGASAYGSL GGPAPPPAPP    60
PPPPPPHSF IKQEPSWGGA EPHEEQCLSA FTVHFSGQFT GTAGACRYGP FGPPPPSQAS   120
SGQARMFPNA PYLPSCLESQ PAIRNQGYST VTFDGTPSYG HTPSHHAAQF PNHSFKHEDP   180
MGQQGSLGEQ QYSVPPPVYG CHTPTDSCTG SQALLLRTPY SSDNLYQMTS QLECMTWNQM   240
NLGATLKGVA AGSSSSVKWT EGQSNHSTGY ESDNHTTPI                          279

SEQ ID NO: 49           moltype = AA   length = 406
FEATURE                 Location/Qualifiers
source                  1..406
                        mol_type = protein
                        organism = Homo sapiens
REGION                  1..406
                        note = Antigen RNF43
SEQUENCE: 49
SGGHQLQLAA LWPWLLMATL QAGFGRTGLV LAAAVESERS AEQKAIIRVI PLKMDPTGKL    60
NLTLEGVFAG VAEITPAEGK LMQSHPLYLC NASDDDNLEP GFISIVKLES PRRAPAHPLI   120
CGPPGLDKRL LPETPGPCYS NSQPVWLCLT PRQPLEPHPP GEGPSEWSSD TAEGRPCPYP   180
HCQVLSAQPG SEEELEELCE QAVSGGHQLQ LAALWPWLLM ATLQAGFGRT GLVLAAAVES   240
```

```
ERSAEQKAII RVIPLKMDPT GKLNLTLEGV FAGVAEITPA EGKLMQSHPL YLCNASDDDN    300
LEPGFISIVK LESPRRAPAH PLICGPPGLD KRLLPETGPG CYSNSQPVWL CLTPRQPLEP    360
HPPGEGPSEW SSDTAEGRPC PYPHCQVLSA QPGSEEELEE LCEQAV                   406

SEQ ID NO: 50           moltype = AA  length = 284
FEATURE                 Location/Qualifiers
source                  1..284
                        mol_type = protein
                        organism = Homo sapiens
REGION                  1..284
                        note = Antigen CEA-NE3
SEQUENCE: 50
KLTIESTPFN VAEGKEVLLL VHNLPQHLFG YSWYKGERVD GNRQIIGYVI GTQQATPGPA     60
YSGREIIYPN ASLLIQNIIQ NDTGFYTLHV IKSDLVNEEA TGQFRVYPEL PKPSISSNNS    120
KPVEDKDAVA FTCEPETQDA TYLWWVNNQS LPVSPRLQLS NGNRTLTLFN VTRNDTASYK    180
CETQNPVSAR RSDSVILNVL YGPDTPIISP PDSSYLSGAN LNLSCHSASN PSPQYSWFVN    240
GTFQQHTQVL LIAKIQPNNN GTYACFVSNL ATGRNNSIVK SITV                    284

SEQ ID NO: 51           moltype = AA  length = 528
FEATURE                 Location/Qualifiers
REGION                  1..528
                        note = Fusion protein CD40L47-261-TPE-E7
source                  1..528
                        mol_type = protein
                        organism = synthetic construct
SEQUENCE: 51
MHRRLDKIED ERNLHEDFVF MKTIQRCNTG ERSLSLLNCE EIKSQFEGFV KDIMLNKEET     60
KKENSFEMQK GDQNPQIAAH VISEASSKTT SVLQWAEKGY YTMSNNLVTL ENGKQLTVKR    120
QGLYYIYAQV TFCSNREASS QAPFIASLCL KSPGRFERIL LRAANTHSSA KPCGQQSIHL    180
GGVFELQPGA SVFVNVTDPS QVSHGTGFTS FGLLKLEFGS ELEAAAAKEA AAAKEAAAAK    240
RARYKRGWEQ LEQCGYPVQR LVALYLAARL SWTMGSSHHH HHHSSGLVPR GSHMHGDTPT    300
LHEYMLDLQP ETTDLYCYEQ LNDSSEEEDE IDGPAGQAEP DRAHYNIVTF CCKCDSTLRL    360
CVQSTHVDIR TLEDLLMGTL GIVCPICSQK PAEAAAAKEA AAAKEAAAAK EAAAAKAHGP    420
KATLQDIVLH LEPQNEIPVD LLCHEQLSDS EEENDEIDGV NHQHLPARRA EPQRHTMLCM    480
CCKCEARIKL VVESSADDLR AFQQLFLNTL SFVCPWCASQ QTRAKDEL                528

SEQ ID NO: 52           moltype = AA  length = 467
FEATURE                 Location/Qualifiers
REGION                  1..467
                        note = Fusion protein 18sCD40L-TPE-E7
source                  1..467
                        mol_type = protein
                        organism = synthetic construct
SEQUENCE: 52
MENSFEMQKG DQNPQIAAHV ISEASSKTTS VLQWAEKGYY TMSNNLVTLE NGKQLTVKRQ     60
GLYYIYAQVT FCSNREASSQ APFIASLCLK SPGRFERILL RAANTHSSAK PCGQQSIHLG    120
GVFELQPGAS VFVNVTDPSQ VSHGTGFTSF GLLKLEFGSE LEAAAAKEAA AAKEAAAAKR    180
ARYKRGWEQL EQCGYPVQRL VALYLAARLS WTMGSSHHHH HHSSGLVPRG SHMHGDTPTL    240
HEYMLDLQPE TTDLYCYEQL NDSSEEEDEI DGPAGQAEPD RAHYNIVTFC CKCDSTLRLC    300
VQSTHVDIRT LEDLLMGTLG IVCPICSQKP AEAAAAKEAA AKEAAAAKE AAAAKAHGPK    360
ATLQDIVLHL EPQNEIPVDL LCHEQLSDSE EENDEIDGVN HQHLPARRAE PQRHTMLCMC    420
CKCEARIKLV VESSADDLRA FQQLFLNTLS FVCPWCASQQ TRAKDEL                 467

SEQ ID NO: 53           moltype = AA  length = 535
FEATURE                 Location/Qualifiers
REGION                  1..535
                        note = Fusion protein E7-TStx-CD40L47-261
source                  1..535
                        mol_type = protein
                        organism = synthetic construct
SEQUENCE: 53
MKLTMGSSHH HHHHSSGLVP RGSHMHGDTP TLHEYMLDLQ PETTDLYCYE QLNDSSEEED     60
EIDGPAGQAE PDRAHYNIVT FCCKCDSTLR LCVQSTHVDI RTLEDLLMGT LGIVCPICSQ    120
KPAEAAAAKE AAAAKEAAAA KEAAAAKAHG PKATLQDIVL HLEPQNEIPV DLLCHEQLSD    180
SEEENDEIDG VNHQHLPARR AEPQRHTMLC MCCKCEARIK LVVESSADDL RAFQQLFLNT    240
LSFVCPWCAS QQTRAPDYHG QDSVRVGRIS FGSINAILGS VALILNCHHH ASRVAREFGS    300
ELEAAAAKEA AAAKEAAAAK HRRLDKIEDE RNLHEDFVFM KTIQRCNTGE RSLSLLNCEE    360
IKSQFEGFVK DIMLNKEETK KENSFEMQKG DQNPQIAAHV ISEASSKTTS VLQWAEKGYY    420
TMSNNLVTLE NGKQLTVKRQ GLYYIYAQVT FCSNREASSQ APFIASLCLK SPGRFERILL    480
RAANTHSSAK PCGQQSIHLG GVFELQPGAS VFVNVTDPSQ VSHGTGFTSF GLLKL         535

SEQ ID NO: 54           moltype = AA  length = 474
FEATURE                 Location/Qualifiers
REGION                  1..474
                        note = Fusion protein E7-TStx-18sCD40L
source                  1..474
                        mol_type = protein
                        organism = synthetic construct
SEQUENCE: 54
```

-continued

```
MKLTMGSSHH HHHHSSGLVP RGSHMHGDTP TLHEYMLDLQ PETTDLYCYE QLNDSSEEED  60
EIDGPAGQAE PDRAHYNIVT FCCKCDSTLR LCVQSTHVDI RTLEDLLMGT LGIVCPICSQ  120
KPAEAAAAKE AAAAKEAAAA KEAAAAKAHG PKATLQDIVL HLEPQNEIPV DLLCHEQLSD  180
SEEENDEIDG VNHQHLPARR AEPQRHTMLC MCCKCEARIK LVVESSADDL RAFQQLFLNT  240
LSFVCPWCAS QQTRAPDYHG QDSVRVGRIS FGSINAILGS VALILNCHHH ASRVAREFGS  300
ELEAAAAKEA AAAKEAAAAK ENSFEMQKGD QNPQIAAHVI SEASSKTTSV LQWAEKGYYT  360
MSNNLVTLEN GKQLTVKRQG LYYIYAQVTF CSNREASSQA PFIASLCLKS PGRFERILLR  420
AANTHSSAKP CGQQSIHLGG VFELQPGASV FVNVTDPSQV SHGTGFTSFG LLKL        474

SEQ ID NO: 55          moltype = AA  length = 541
FEATURE                Location/Qualifiers
REGION                 1..541
                       note = Fusion protein HBx-preS1-TStx-18sCD40L
source                 1..541
                       mol_type = protein
                       organism = synthetic construct
SEQUENCE: 55
MKLTMGSSHH HHHHSSGLVP RGSHMAARMC CQLDPARDVL CLRPVGAESR GRPLPGPLGA  60
LPPSSASAVP ADHGSHLSLR GLPVCSFSSA GPCALRFTSA RRMETTVNAP WSLPTVLHKR  120
TIGLSGRSMT WIEEYIKDCV FKDWEELGEE IRLKVFVLGG CRHKLVCSPA PCNFFTSARG  180
RAEAAAAKEA AAAKEAAAAK EAAAAKAEFM GGWSSKPRQG MGTNLSVPNP LGFFPDHQLD  240
PAFGANSNNP DWDFNPNKDH WPEANQVGAG AFGPGFTPPH GGLLGWSPQA QGILTTVPAA  300
PPPASTNRQS GRQPTPIELT RAPDYHGQDS VRVGRISFGS INAILGSVAL ILNCHHHASR  360
VAREFGSELE AAAAKEAAAA KEAAAAKENS FEMQKGDQNP QIAAHVISEA SSKTTSVLQW  420
AEKGYYTMSN NLVTLENGKQ LTVKRQGLYY IYAQVTFCSN REASSQAPFI ASLCLKSPGR  480
FERILLRAAN THSSAKPCGQ QSIHLGGVFE LQPGASVFVN VTDPSQVSHG TGFTSFGLLK  540
L                                                                 541

SEQ ID NO: 56          moltype = AA  length = 6
FEATURE                Location/Qualifiers
REGION                 1..6
                       note = Rigid linker 1 with n=1
source                 1..6
                       mol_type = protein
                       organism = synthetic construct
SEQUENCE: 56
EAAAAK                                                            6
```

What is claimed is:

1. A fusion protein comprising:

(a) a CD40-binding domain, which is a CD40 ligand (CD40L) or a functional fragment thereof comprising an amino acid sequence that is at least 90% identical to SEQ ID NO: 19, said CD40L or functional fragment thereof consists of 154-261 amino acids in length;

(b) an antigen, which is a tumor antigen or an antigen of a pathogen, being located at the N-terminal of the fusion protein;

(c) a translocation domain, located between the CD40-binding domain and the antigen, said translocation domain being a Shiga toxin (Stx) translocation peptide; and (d) a furin and/or cathepsin L cleavage site, located between the CD40-binding domain and the translocation domain.

2. The fusion protein of claim 1, wherein the Stx translocation peptide comprises an amino acid sequence that is at least 90% identical to the amino acid sequence selected from the group consisting of SEQ ID NOs: 12, 13, 14, 15 and 16, with 8-84 amino acid residues in length.

3. The fusion protein of claim 1, wherein the Stx translocation peptide comprises an amino acid sequence of SEQ ID NO: 12 with 8-84 amino acids in length.

4. The fusion protein of claim 1, wherein the furin and/or cathepsin L cleavage site permits removal of the CD40-binding domain away from the fusion protein via furin and/or cathepsin L cleavage.

5. The fusion protein of claim 1, wherein the furin and/or cathepsin L cleavage site comprises an amino acid sequence of $RX^1X^2R$, wherein $X^1$ and $X^2$ are any amino acids, or comprise an amino acid sequence of $RX^1RX^2X^3R$, wherein $X^1$ and $X^2$ are any amino acids and $X^3$ is K, F or R.

6. The fusion protein of claim 1, further comprising a peptide linker, said peptide linker comprising the furin and/or cathepsin L cleavage site located between the CD40-binding domain and the translocation domain.

7. The fusion protein of claim 1, wherein the antigen is a tumor antigen, said tumor being selected from the group consisting of breast cancer, colon cancer, rectal cancer, bladder cancer, endometrial cancer, kidney cancer, gastric cancer, glioblastoma, hepatocellular carcinoma, bile duct cancer, small cell lung cancer, non-small cell lung cancer (NSCLC), melanoma, ovarian cancer, cervical cancer, pancreatic cancer, prostate cancer, acute myelogenous leukemia (AML), chronic myelogenous leukemia (CML), non-Hodgkin's lymphoma, and thyroid cancer.

8. The fusion protein of claim 1, wherein the antigen is an antigen of a pathogen, said pathogen being selected from the group consisting of Human Papillomavirus (HPV), Human Immunodeficiency Virus-1 (HIV-1), Influenza Virus, Dengue Virus, Hepatitis A Virus (HAV), Hepatitis B Virus (HBV), Hepatitis C Virus (HCV), Hepatitis D Virus (HDV), Hepatitis E Virus (HEV), Severe acute respiratory syndrome-associated coronavirus (SARS-COV), Severe acute respiratory syndrome coronavirus 2 (SARS-COV-2), Middle East respiratory syndrome coronavirus (MERS-COV), Epstein-Barr virus (EBV), Zika Virus, Rabies Virus, Variola virus, Chikungunya Virus, West Nile virus, Poliovirus, Measles virus, Rubella virus, Hantavirus, Japanese encephalitis virus, Coxsackievirus, Echovirus, Enterovirus, Mumps virus, Varicella-zoster virus (VZV), Cercopithecine herpesvirus-1 (CHV-1), Yellow fever virus (YFV), Rift Valley Fever Virus, Lassa virus, Marburg virus, Ebolavirus, Norovirus, Rotavirus, Adenovirus, Sapovirus, Astrovirus, *Rickettsia prowazekii, Rickettsia typhi, Orientia tsutsugamushi, Borrelia burgdorferi, Yersinia pestis, Plasmodium vivax, Plasmodium malariae, Plasmodium falciparum, Plasmodium ovale, Bacillus anthracis, Clostridium Difficile, Clostridium Botulinum, Corynebacterium diphtheriae, Salmonella enterica* serovar Typhi, *Salmonella enterica* serovar Paratyphi A, Shiga toxin-producing *E. coli* (STEC), *Shigella dysenteriae, Shigella flexneri, Shigella boydii, Shigella sonnei, Entamoeba histolytica, Vibrio cholerae, Mycobacterium tuberculosis, Neisseria meningitidis, Bordetella pertusis, Haemophilus influenzae* type B (HiB), *Clostridium tetani, Listeria monocytogenes* and *Streptococcus pneumoniae.*

9. The fusion protein of claim 2, wherein the Stx translocation peptide comprises an amino acid sequence selected from the group consisting of SEQ ID NOs: 12, 13, 14, 15 and 16.

10. A fusion protein comprising:
(a) a CD40-binding domain, which is a CD40 ligand (CD40L) or a functional fragment thereof comprising an amino acid sequence that is at least 90% identical to SEQ ID NO: 19, said CD40L or functional fragment thereof consists of 154-261 amino acids in length;
(b) an antigen, which is a tumor antigen or an antigen of a pathogen, being located at the N-terminal of the fusion protein;
(c) a translocation domain, located between the CD40-binding domain and the antigen, said translocation domain being a Shiga toxin (Stx) translocation peptide, comprising an amino acid sequence of SEQ ID NO: 12; and
(d) a furin and/or cathepsin L cleavage site, located between the CD40-binding domain and the translocation domain.

11. The fusion protein of claim 10, wherein the Stx translocation peptide comprises an amino acid sequence selected from the group consisting of SEQ ID NOs: 12, 13, 14, 15 and 16.

12. The fusion protein of claim 10, wherein the CD40L or the functional fragment thereof comprises the amino acid sequence of SEQ ID NO: 18 or SEQ ID NO: 19.

13. The fusion protein of claim 1, wherein the CD40L or the functional fragment thereof comprises the amino acid sequence of SEQ ID NO: 18 or SEQ ID NO: 19.

14. The fusion protein of claim 1, wherein the CD40-binding domain or the functional fragment thereof consists of the amino acid sequence of SEQ ID NO: 19.

15. The fusion protein of claim 1, which comprises the amino acid sequence selected from the group consisting of SEQ ID NOs: 53, 54 and 55.

16. The fusion protein of claim 10, which comprises the amino acid sequence selected from the group consisting of SEQ ID NOs: 53, 54 and 55.

17. A method for eliciting an antigen-specific cell-mediated immune response, comprising:
administering a therapeutically effective amount of the fusion protein of claim 1 to a subject in need thereof, and thereby eliciting the antigen-specific cell-mediated immune response in the subject in need thereof.

18. A method for eliciting an antigen-specific cell-mediated immune response, comprising:
administering a therapeutically effective amount of the fusion protein of claim 10 to a subject in need thereof, and thereby eliciting the antigen-specific cell-mediated immune response in the subject in need thereof.

19. A method for treating a tumor or a disease caused by a pathogen in a subject in need thereof, comprising:
administering to the subject in need thereof a therapeutically effective amount of the fusion protein of claim 1, wherein the antigen of the fusion protein is the tumor antigen, and thereby treating the subject in need thereof.

20. A method for treating a tumor or a disease caused by a pathogen in a subject in need thereof, comprising:
administering to the subject in need thereof a therapeutically effective amount of the fusion protein of claim 10, wherein the antigen of the fusion protein is the antigen of the pathogen, and thereby treating the disease caused by the pathogen.

\* \* \* \* \*